(12) United States Patent
Björ et al.

(10) Patent No.: US 6,887,881 B1
(45) Date of Patent: May 3, 2005

(54) BISPIDINE COMPOUNDS USEFUL IN THE TREATMENT OF CARDIAC ARRYTHMIAS

(75) Inventors: Annika Björ, Stenungsund (SE);
Magnus Björsne, Västra Frölunda (SE);
Torbjörn Halvarsson, Vallda (SE);
Kurt-Jürgen Hoffmann, Kullavik (SE);
Bertil Samuelsson, Skärholmen (SE);
Gert Strandlund, Lindome (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/623,709

(22) PCT Filed: Jun. 15, 2000

(86) PCT No.: PCT/SE00/01253

§ 371 (c)(1),
(2), (4) Date: Sep. 7, 2000

(87) PCT Pub. No.: WO00/76999

PCT Pub. Date: Dec. 21, 2000

(30) Foreign Application Priority Data

Jun. 16, 1999 (SE) ............................................... 9902270

(51) Int. Cl.$^7$ .................. C07D 471/08; A61K 31/4748; A61P 9/06

(52) U.S. Cl. ......................... 514/278; 514/300; 546/18; 546/122

(58) Field of Search ................................ 514/300, 278; 546/122, 18

(56) References Cited

U.S. PATENT DOCUMENTS

| 3,962,449 A | 6/1976 | Binnig et al. |
| 4,459,301 A | 7/1984 | Binnig et al. |
| 4,550,112 A | 10/1985 | Schoen et al. |

(Continued)

FOREIGN PATENT DOCUMENTS

| EP | 0 306 871 A2 | 3/1989 |
| EP | 0 308 848 A2 | 3/1989 |
| EP | 0 665 228 A1 | 8/1995 |
| WO | 308843 | 3/1989 |
| WO | 91/07405 | 5/1991 |
| WO | 97/17961 | 5/1997 |
| WO | 99/31100 | 6/1999 |
| WO | 00/61569 | 10/2000 |
| WO | 00/71529 | 11/2000 |

OTHER PUBLICATIONS

The IUPAC Acyclic Hydrocarbons Rules A–1.2 and A–3.5.*
The Academic Press Dictionary of Science and Technology definition for alkyl <http://www.harcourt.com/dictionary/def/3/7/6/7/376700.html>downloaded from the internet Mar. 14, 2002.*
Hawley's Condensed Chemical Dictionary, 13th edition (1977) p. 34.*

Encarta® World English Dictionary definition for alkyl <http://dictionary.msn.com/find/print/asp?refid=1861584705&search=alkyl&ww=2464>(downloaded from the Internet Mar. 14, 2002).*

Hackh's Chemical Dictionary, 3rd edition page 33 (1944).*

On–line Medical Dictionary definition for alkyl <http://cancerweb.ncl.ac.uk/cgi–bin/omd?query=alkyl&action=Search+OMD> (downloaded from the Internet Sep. 4, 2002).*

March, Advanced Organic Chemistry, Third edition, apges 222, 507–508, 983–989.*

J. March "Advanced Organic Chemistry" 3rd Edition (Wiley & sons 1985) p. 1100.

Paroczai et al, "Investigations to Characterize a New. . . ," Pharmacological Research, vol. 24, No. 2, pp. 149–162 (1991).

Chen et al, "High–Performance Liquid . . . ," Analytical Sciences, vol. 9, pp. 429–451 (1993).

Garrison et al, "Novel 3,7–Diheterabicyclo[3.3.1]nonanes. . . ," J. Med. Chem., vol. 39, pp. 2559–2570 (1996).

Wang et al, "Class III Antiarrhythmic Drug Action. . . ," Circulation, vol. 90, No. 4, pp. 2032–2040 (1994).

Villa et al, "3,8–Diazabicyclo . . . ," Eur. J. Med. Chem., vol. 36, pp. 495–506 (2001).

*Primary Examiner*—Mark L. Berch
(74) *Attorney, Agent, or Firm*—Nixon & Vanderhye

(57) ABSTRACT

There is provided compounds of formula I,

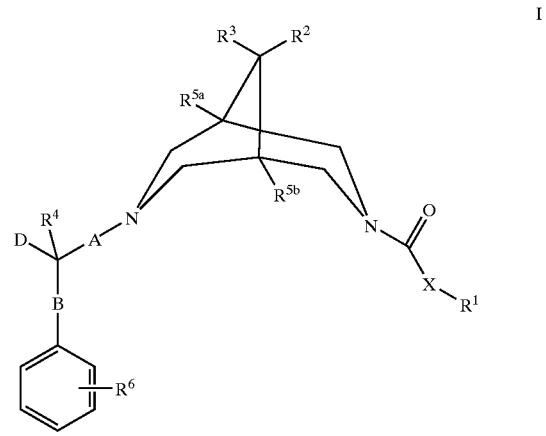

wherein $R^1$, $R^2$, $R^3$, $R^4$, $R^{5a}$, $R^{5b}$, $R^6$, X, A, B and D have meanings given in the description, which are useful in the prophylaxis and in the treatment of arrhythmias, in particular atrial and ventricular arrhythmias.

22 Claims, No Drawings

U.S. PATENT DOCUMENTS

| | | |
|---|---|---|
| 4,556,662 A | 12/1985 | Binnig et al. |
| 4,912,113 A | 3/1990 | Schon et al. |
| 4,959,373 A | 9/1990 | Lubisch et al. |
| 5,468,858 A | 11/1995 | Berlin et al. |
| 5,576,327 A | 11/1996 | Schoen et al. |
| 5,786,481 A | 7/1998 | Berlin et al. |
| 6,255,301 B1 * | 7/2001 | Gustafsson et al. .... 514/210.17 |
| 6,291,475 B1 * | 9/2001 | Alstermark et al. ........ 514/300 |
| 6,407,114 B1 * | 6/2002 | Bunnage et al. .......... 514/262.1 |
| 6,465,481 B1 * | 10/2002 | Frantsi et al. ................ 514/300 |
| 6,492,382 B1 * | 12/2002 | Bjore et al. .................. 514/300 |
| 6,559,143 B1 * | 5/2003 | Bjore et al. ............... 514/230.5 |
| 2003/0212095 A1 * | 11/2003 | Andersson et al. .......... 514/300 |
| 2004/0229900 A1 * | 11/2004 | Schrimpf .................... 514/300 |

* cited by examiner

BISPIDINE COMPOUNDS USEFUL IN THE TREATMENT OF CARDIAC ARRYTHMIAS

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in New England Journal of Medicine, 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (tuning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent application WO 91/07405, European patent applications 306 871, 308 843 and 665 228 and U.S. Pat. Nos. 3,962,449, 4,556,662, 4,550,112, 4,459,301 and 5,468,858, as well as journal articles including inter alia J. Med. Chem. 39, 2559, (1996), Pharmacol. Res., 24, 149 (1991), Circulation, 90, 2032 (1994) and Anal. Sci. 9, 429, (1993). Known bispidine-based antiarrhythmic compounds include bisaramil (3-methyl-7-ethyl 9α,4'-(Cl-benzoyloxy)-3,7-diazabicyclo[3.3.1]nonane), tedisamil (3',7'-bis (cyclopropylmethyl)spiro-(cyclopentane-1,9')-3,7-diazabicyclo[3.3.1]nonane), SAZ-VII-22(3-(4-chlorobenzoyl)-7-isopropyl-3,7-diazabicyclo[3.3.1]nonane), SAZ-VII-23 (3-benzoyl-7-isopropyl-3,7-diazabicyclo[3.3.1]nonane), GLG-V-13 (3-[4-(1H-imidazol-1-yl)benzoyl]-7-isopropyl-3,7-diazabicyclo[3.3.1]nonane), KMC-IV-84 (7-[4'-(1H-imidazolo 1-yl)benzenesulfonyl]-3-isopropyl-3,7-diazabicyclo[3.3.1]nonane dihydroperchiorate and ambasilide (3-(4-aminobenzoyl)-7-benzyl-3,7-diazabicyclo[3.3.1]nonane).

We have surprisingly found that a novel group of bispidine-based compounds exhibit electrophysiological activity, preferably class III electrophysiological activity, and are therefore expected to be useful in the treatment of cardiac arrhythmias.

DISCLOSURE OF THE INVENTION

According to the invention there is provided compounds of formula I,

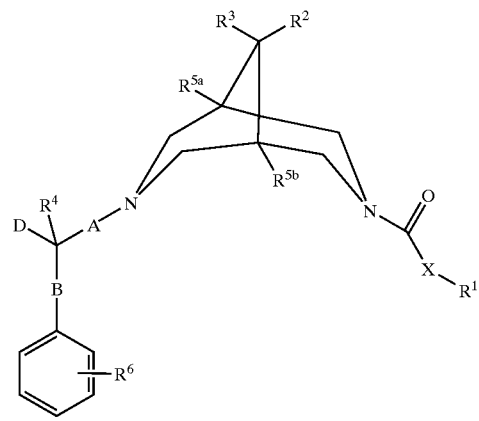

wherein
$R^1$ represents $C_{1-12}$ alkyl, —$(CH_2)_a$-aryl, or —$(CH_2)_a$-$Het^1$ (all of which are optionally substituted and/or terminated (as appropriate) by one or more substituents selected from —OH, halo, cyano, nitro, $C_{1-4}$ alkyl and/or $C_{1-4}$ is alkoxy);
a represents 0, 1, 2, 3, or 4;
$Het^1$ represents a five to ten-membered heterocyclic ring containing one or more heteroatoms selected from oxygen, nitrogen and/or sulfur, and which also optionally includes one or more =O substituents;
X represents O or S;
$R^{5a}$ and $R^{5b}$ independently represent H or $C_{1-3}$ alkyl;
$R^2$ and $R^3$ independently represent H, $C_{1-4}$ alkyl (optionally substituted and/or terminated with one or more nitro or cyano groups), $OR^7$, $N(R^{7a})R^{7b}$, $OC(O)R^8$ or together form —O—$(CH_2)_2$—O—, —$(CH_2)_3$—, —$(CH_2)_4$— or —$(CH_2)_5$—;
$R^7$ and $R^8$ independently represent H, $C_{1-6}$ alkyl or —$(CH_2)_b$-aryl (which latter two groups are optionally substituted and/or terminated by one or more substituents selected from —OH, halo, cyano, nitro, $C_{1-4}$ alkyl and/or $C_{1-4}$, alkoxy);
$R^{7a}$ and $R^{7b}$ independently represent H or $C_{1-6}$ alkyl;
b represents 0, 1, 2, 3 or 4;
$R^4$ represents H or $C_{1-6}$ alkyl;
D represents H, $C_{1-4}$ alkyl, —OH, or —$(CH_2)_c$$N(R^{10})(R^{11})$;
c represents 0, 1, 2, 3 or 4;
$R^{10}$ represents H, $C_{1-4}$ alkyl, —$(CH_2)_d$-aryl, —$C(NH)NH_2$, —$S(O)_2R^{13}$, —$[C(O)]_eN(R^{14})(R^{15})$, —$C(O)R^{16}$ or —$C(O)OR^{17}$; e represents 1 or 2;
$R^{11}$ represents H, $C_{1-6}$ alkyl, —$C(O)R^{18}$ or —$(CH_2)_f$aryl (which latter group is optionally substituted and/or terminated (as appropriate) by one or more substituents selected from —OH, cyano, halo, amino, nitro, $C_{1-4}$ alkyl and/or $C_{1-4}$ alkoxy);
$R^{14}$, $R^{15}$, $R^{16}$, $R^{17}$ and $R^{18}$ independently represent H, $C_{1-4}$ alkyl, $Het^2$ or —$(CH_2)_g$-aryl (which latter three groups are optionally substituted and/or terminated (as appropriate) by one or more substituents selected from —OH, cyano, halo, amino, nitro, $C_{1-4}$ alkyl and/or $C_{1-6}$ alkoxy);

$R^{13}$ represents $C_{1-6}$, alkyl, aryl or —$(CH_2)_h$-aryl (all of which are all optionally substituted and/or terminated (as appropriate) by one or more substituents chosen from halo, nitro, $C_{1-6}$ alkyl and/or $C_{1-4}$ alkoxy); d, f, g and h independently represent 0, 1, 2, 3 or 4; Het² represents a five to ten-membered heterocyclic ring containing one or more heteroatoms selected from oxygen, nitrogen and/or sulfur, and which also optionally includes one or more =O substituents;

$R^6$ represents one or more optional substituents selected from —OH, cyano, halo, amino, nitro, $C_1$, alkyl (optionally terminated by —N(H)C(O)OR$^{18a}$), $C_{1-6}$ alkoxy, —C(O)N(H)R$^{19}$, —NHC(O)N(H)R$^{20}$, —N(H)S(O)$_2$R$^{21}$ and/or —OS(O)$_2$R$^{22}$;

$R^{19}$ and $R^{20}$ independently represent H or $C_{1-6}$ alkyl;

$R^{18a}$, $R^{21}$ and $R^{22}$ independently represent $C_{1-4}$ alkyl; A represents a single bond, $C_{1-6}$ alkylene, —N(R$^{23}$)(CH$_2$)$_n$—, —O(CH$_2$)$_j$— or —(CH$_2$)$_j$C(H)(OR$^{23}$)(CH$_2$)$_k$— (in which latter three groups, the —(CH$_2$)$_j$— group is attached to the bispidine nitrogen atom, and which latter four groups are all optionally substituted by one or more OH groups);

B represents a single bond, $C_{1-4}$ alkylene, —(CH$_2$)$_m$N(R$^{24}$)—, —(CH$_2$)$_m$S(O)$_n$—, —(CH$_2$)$_m$O— (in which three latter groups, the —(CH$_2$m— group is attached to the carbon atom bearing D and R$^4$), —C(O)N(R$^{24}$)— (in which latter group, the —C(O)— group is attached to the carbon atom bearing D and R$^4$), —N(R$^{24}$)C(O)O(CH$_2$)$_m$— or —N(R$^{24}$)(CH$_2$)$_m$— (in which latter two groups, the N(R$^{24}$) group is attached to the carbon atom bearing D and R$^4$); j, k and m independently represent 0, 1, 2, 3 or 4;

n represents 0, 1 or 2;

$R^{23}$ represents H, $C_1$, alkyl or C(O)R$^{25}$;

$R^{24}$ represents H or $C_{1-6}$ alkyl;

$R^{25}$ represents H, $C_{1-6}$ alkyl, Het³ or —(CH$_2$)$_p$-aryl (which latter two groups are optionally substituted and/or terminated (as appropriate) by one or more substituents selected from —OH, cyano, halo, amino, nitro, $C_{1-4}$ alkyl and/or $C_{1-6}$ alkoxy);

Het³ represents a five to ten-membered heterocyclic ring containing one or more heteroatoms selected from oxygen, nitrogen and/or sulfur, and which also optionally includes one or more =O substituents;

p represents 0, 1, 2, 3 or 4;

or a pharmaceutically acceptable derivative thereof.

provided that:
(a) when D represents either H or —OH, and R$^{5a}$ and R$^{5b}$ both represent H, then at least one of R² and R³ represents OR$^7$, OC(O)R$^8$ or $C_{1-4}$ alkyl, which alkyl group is substituted and/or terminated with one or more nitro or cyano groups; and
(b) when D represents —OH or —(CH$_2$)$_c$N(R$^1$) R$^{11'}$ in which c represents 0, then:—
  (i) A does not represent —N(R$^{23}$)(CH$_2$)$_j$—, —O(CH$_2$)$_j$— or —(CH$_2$)$_j$C(H)(OR$^{23}$)(CH$_2$)$_k$— (in which k is 0); and/or
  (ii) m does not represent 0 when B represents —(CH$_2$)$_n$N(R$^{24}$)—, -(CH$_2$)$_m$S(O)$_n$, or —(CH$_2$)$_m$O—, which compounds are referred to hereinafter as "the compounds of the invention".

Aryl groups that may be mentioned include $C_{6-10}$ aryl groups, such as phenyl, naphthyl and the like. Oxyaryl groups that may be mentioned include $C_{6-10}$ oxyaryl groups, such as oxyphenyl (phenoxy), oxynaphthyl (naphthoxy) and the like. When substituted, aryl and aryloxy groups are preferably substituted by between one and three substituents. Het¹, Het² and Het³ groups that may be mentioned include those containing 1 to 4 heteroatoms (selected from the group oxygen, nitrogen and/or sulfur) and in which the total number of atoms in the ring system is between five and ten. Het (Het¹, Het² and Het³) groups may be wholly/partly aromatic in character and may be bicyclic. Heterocyclic groups that may be mentioned include morpholinyl, thiazolyl, oxazolyl, isoxazolyl, cinnolinyl, quinazolinyl, phthalazinyl, purinyl, benzimidazolyl, pyrimindinyl, piperazinyl, pyrazinyl, piperidinyl, pyridinyl, pyrrolinyl, pyrrolidinyl, pyrollidinonyl, triazolyl, imidazolyl, quinolinyl, isoquinolinyl, dioxanyl, benzodioxanyl, benzodioxolyl, benzodioxepanyl, benzomorpholinyl, indolyl, pyrazolyl, pyrrolyl, benzothiophenyl, thiophenyl, chromanyl, thiochromanyl, benzofuranyl, pyranyl, tetrahydropyranyl, tetrahydrofuranyl, furanyl and the like. Values of Het² that may be mentioned include pyrollidinonyl (e.g. 2-pyrrolidinon-5-yl). Substituents on Het (Het¹, Het² and Het) groups may, where appropriate, be located on any atom in the ring system including a heteroatom. The point of attachment of Het (Het¹, Het² and Het³) groups may be via any atom in the ring system including (where appropriate) a heteroatom. Het (Het¹, Het² and Het³) groups may also optionally be in the N— or S—oxidised form.

Pharmaceutically acceptable derivatives include salts and solvates. Salts which may be mentioned include acid addition salts. Pharmaceutically acceptable derivatives also include $C_{1-4}$ alkyl quaternary ammonium salts and N-oxides, provided that, when a N-oxide is present:
(a) no Het (Het¹, Het², Het³) groups contain an unoxidised S-atom;
(b) X does not represent S; and/or
(c) n does not represent 0, when B represents —(CH$_2$)$_m$S(O)$_n$—.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Alkyl groups that R¹, R², R³, R⁴, R$^{5a}$, R$^{5b}$, R⁶, R⁷, R$^{7a}$, R$^{7b}$, R⁸, R$^{10}$, R$^{11}$, R$^{13}$, R$^{14}$, R$^{15}$, R$^{16}$, R$^{17}$, R$^{18}$, R$^{8a}$, R$^{19}$, R$^{20}$, R$^{21}$, R$^{22}$, R$^{23}$, R$^{24}$, R$^{25}$ and D may represent, and with which R¹, R⁷, R⁸, R$^{11}$, R$^{13}$, R$^{14}$, R$^{15}$, R$^{16}$, R$^{17}$, R$^{18}$ and R$^{25}$ may be substituted; and alkoxy groups that R⁶ may represent, and with which R¹, R⁷, R¹, R$^{11}$, R$^{13}$, R$^{14}$, R$^{15}$, R$^{16}$, R$^{17}$, R$^{18}$ and R$^{25}$ may be substituted, may be linear or, when there is a sufficient number (i.e. three) of carbon atoms, be branched and/or cyclic. Further, when there is a sufficient number (i.e. four) of carbon atoms, such alkyl and alkoxy groups may also be part cyclic/acyclic. Such alkyl and alkoxy groups may also be saturated or, when there is a sufficient number (i.e. two) of carbon atoms, be unsaturated and/or interrupted by oxygen and/or substituted by one or more fluoro groups.

Alkylene groups that A and B may represent, and —(CH$_2$)— containing groups that R$^1$, R$^2$ and R$^3$ (together), R$^7$, R$^8$, R$^{10}$, R$^{11}$, R$^{13}$, R$^{14}$, R$^{15}$, R$^{16}$, R$^{17}$, R$^{18}$, R$^{25}$, A, B and D may include, may be linear or, when there is a sufficient number (i.e. two) of carbon atoms, be branched. Such alkylene groups and —(CH$_2$)— containing chains may also be saturated or, when there is a sufficient number (i.e. two) of carbon atoms, be unsaturated and/or interrupted by oxygen.

As used herein, the term "halo" includes fluoro, chloro, bromo or iodo.

Abbreviations are listed at the end of this specification.

According to a further aspect of the invention there is provided compounds of formula I as hereinbefore defined, but with the further provisos that:
(a) when A represents —N(R$^{23}$)(CH$_2$)$_j$— or —O(CH$_2$)$_j$—, then j does not represent 0 or 1; and
(b) when D represents —OH or —(CH$_2$)$_n$N(R$^{10}$)R$^{11}$ in which c represents 0, then B does not represent —N(R$^{24}$)C(O)O(CH$_2$)$_m$— or —N(R$^{24}$)(CH$_2$)$_m$—.

Preferred compounds of the invention include those in which:
R$^1$ represents optionally substituted —(CH$_2$)$_a$-phenyl, in which a is 0, 1, 2 or 3, or optionally substituted, optionally unsaturated, linear, branched or cyclic, C$_{1-18}$ alkyl (which latter group may also be interrupted by an oxygen atom);
R$^2$ represents H, OR$^7$, —CH$_2$NO$_2$, —OC(O)R$^8$, or together with R$^3$ represents —O—(CH$_2$)$_2$—O—;
R$^3$ represents H, OR$^7$, C$_{1-4}$ alkyl or together with R$^2$ represents —O—(CH$_2$)$_2$—O—;
R$^4$ represents H or C$_{1-2}$ alkyl;
R$^{5a}$ and R$^{5b}$ either both represent H or both represent methyl;
R$^6$ represents one or more substituents selected from C$_{1-6}$ alkyl, cyano, nitro, amino or C(O)N(H)R$^{19}$ or —N(H)S(O)$_2$R$^{21}$;
X represents 0;
A represents a single bond or linear, or branched, C$_{1-4}$ alkylene (which group is also optionally interrupted by O);
B represents a single bond, C$_{1-4}$ alkylene, —(CH$_2$)$_m$O— or —(CH$_2$)$_m$N(R$^{24}$)— (in which latter two cases m is 1, 2 or 3);
when the bispidine nitrogen bearing A optionally bears a C$_{1-4}$ alkyl group, thus forming a quaternary ammonium salt, the alkyl group is a methyl group.

When D represents —(CH$_2$)$_c$N(R$^{10}$)(R$^{11}$), preferred compounds of the invention include those in which: c represents 0, 1 or 2;
R$^{10}$ represents H, C$_{1-4}$ alkyl, —C(O)R$^{16}$ (in which R$^{16}$ is H, C$_{1-3}$ alkyl or Het$^2$), —C(O)OR$^{17}$ (in which R$^{17}$ is C$_{1-5}$ alkyl, phenyl or C$_{1-3}$ alkylphenyl), —C(NH)NH$_2$ or —[C(O)]$\alpha$-N(H)R$^{15}$ (in which R$^{15}$ is H or C$_{1-3}$ alkyl); R$^{11}$ represents H.

More preferred compounds of the invention include those in which: R$^1$ represents phenyl, C$_{1-2}$ alkylphenyl or linear or branched C$_{2-6}$ alkyl (all of which are optionally substituted with one or more cyano, methyl and/or halo groups);
R$^2$ represents H, OR$^7$ (in which R$^7$ is H or C$_{1-2}$ alkyl), —CH$_2$NO$_2$ or —OC(O)R$^3$ (in which R$^8$ is C$_{1-3}$ alkyl or optionally substituted phenyl);
R$^3$ represents H, OR$^7$ (in which R$^7$ is H or C$_{1-2}$ alkyl) or methyl;
R$^4$ represents methyl or, preferably, H;
R$^6$ represents cyano, preferably in the para position relative to B;

A represents a single bond or C$_{1-2}$ alkylene (e.g. —CH$_2$—);
B represents a single bond, —(CH$_2$)$_m$N(H)— or —(CH$_2$)$_m$O— (in which latter two cases m is 1 or 2); and
D represents H, OH, —CH$_2$NH$_2$, —NHR$^{10}$ (in which R$^{10}$ is H, C$_{1-2}$ alkyl, —C(O)H, —[C(O)]$_2$NH$_2$, —C(NH)NH$_2$, —C(O)N(H)R$^{15}$ (where R$^{15}$ is H or C$_{1-2}$ alkyl), —C(O)[2-pyrrolidon-5-yl] or —C(O)OR$^{17}$ (in which R$^{17}$ is C$_{1-4}$ alkyl or benzyl)).

Preferred compounds of the invention include the compounds of the Examples described hereinafter.

Preparation

According to the invention there is also provided a process for the preparation of compounds of formula I which comprises:

(a) reaction of a compound of formula II,

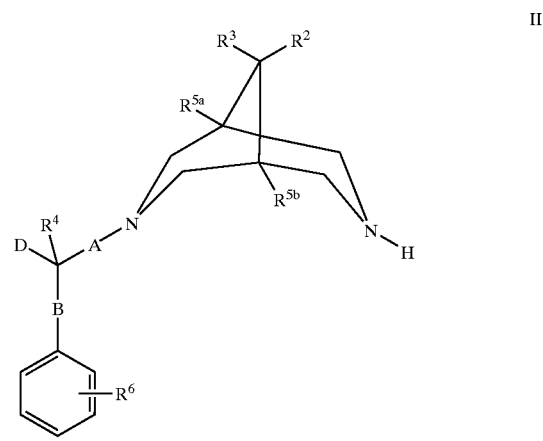

II wherein R$^2$, R$^3$, R$^4$, R$^{5a}$, R$^{5b}$, R$^6$, A, B and D are as hereinbefore defined with a compound of formula III,

R$^1$XC(O)L$^1$      III wherein L$^1$ represents a leaving group, such as Hal, imidazolyl or —OC(O)XR$^1$, Hal represents Cl, Br or I, and R$^1$ and X are as hereinbefore defined, for example at or above room temperature in the presence of a suitable base (e.g. aqueous NaOH, K$_2$CO$_3$ or triethylamine) and an appropriate organic solvent (e.g. CH$_2$Cl$_2$, THF, acetonitrile, toluene, or mixtures of such solvents);

(b) for compounds of formula I in which A represents CH$_2$ and D represents —OH or N(H)R$^{10}$, reaction of a compound of formula IV,

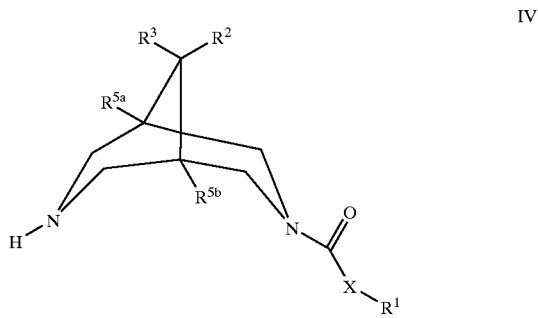

IV wherein R$^1$, R$^2$, R$^3$, R$^{5a}$, R$^{5b}$ and X are as hereinbefore defined, with a compound of formula V,

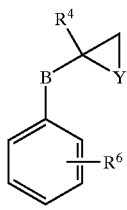

wherein Y represents O or N(R$^{10}$) and R$^4$, R$^6$, R$^{10}$ and B are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(c) reaction of a compound of formula IV, as hereinbefore defined, with a compound of formula VI,

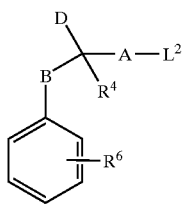

wherein L$^2$ represents a leaving group (e.g. mesylate, tosylate or Hal, where Hal is as hereinbefore defined) and R$^4$, R$^6$, A, B and D are as hereinbefore defined, for example at elevated temperature (e.g. between 35° C. and reflux temperature) in the presence of a suitable base (e.g. triethylamine or K$_2$CO$_3$) and an appropriate organic solvent (e.g. acetonitrile or dimethylsulfoxide);

(d) for compounds of formula I in which D represents H or OH and R$^4$ represents H, reduction of a compound of formula VII,

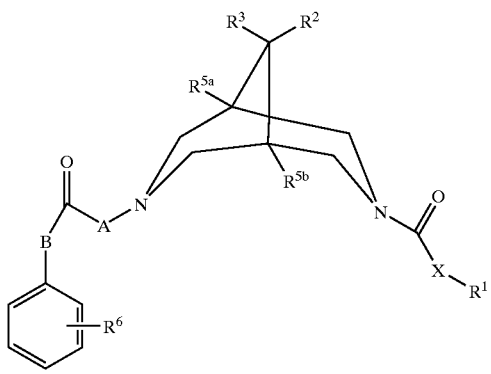

wherein R$^1$, R$^2$, R$^3$, R$^{5a}$, R$^{5b}$, R$^6$, A, B and X are as hereinbefore defined, in the presence of a suitable reducing agent and under appropriate reaction conditions; for example, for formation of compounds of formula I in which D represents —OH, reduction may be performed under mild reaction conditions in the presence of e.g. sodium borohydride and an appropriate organic solvent (e.g. THF); and for formation of compounds of formula I in which D represents H, reduction may be performed by activating the relevant C=O group using an appropriate agent (such as tosylhydrazine) in the presence of a suitable reducing agent (e.g. sodium borohydride or sodium cyanoborohydride) and an appropriate organic solvent (e.g. a lower alkyl alcohol);

(e) for compounds of formula I in which R$^2$ and R$^3$ both represent H, reduction of a corresponding compound of formula VIII,

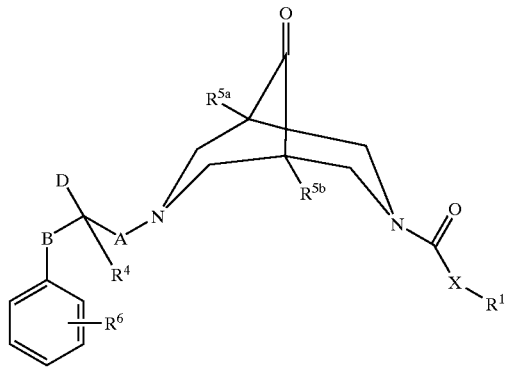

wherein R$^1$, R$^4$, R$^{5a}$, R$^{5b}$, R$^6$, A, B, D and X are as hereinbefore defined, and in which the bridgehead C=O group may be activated using an appropriate agent, such as tosylhydrazine, in the presence of a suitable reducing agent (e.g. sodium borohydride or sodium cyanoborohydride) and an appropriate organic solvent (e.g. a lower alkyl alcohol), or under standard Wolff-Kischner conditions known to those skilled in the art; when the C=O group is activated, the activation step may be carried out at between room and reflux temperature in the presence of an appropriate organic solvent (e.g. a lower alkyl alcohol such as methanol, ethanol or IPA), whereafter the reducing agent may be added to the reaction mixture and the reduction carried out at between 60° C. and reflux, advantageously in the presence of a suitable organic acid (e.g. acetic acid);

(f) for compounds of formula I in which one of R$^2$ and R$^3$ represents H and the other represents —OH, reduction of a corresponding compound of formula VIII, as hereinbefore defined, in the presence of a mild reducing agent, e.g. sodium borohydride, and an appropriate organic solvent (e.g. a lower alcohol such as methanol or ethanol);

(g) for compounds of formula I in which R$^2$ and/or R$^3$ represents OC(O)R$^8$ and R$^1$ is as hereinbefore defined, coupling of a corresponding compound of formula I in which R$^2$ and/or R$^3$ (as appropriate) represents OH and a compound of formula VIIIA,

R$^8$CO$_2$H  VIIIA wherein R$^8$ is as hereinbefore defined, for example at ambient temperature (e.g. 25° C.) in the presence of a suitable coupling agent (e.g. 1-(3-dimethylaminopropyl)-3-ethylcarbodiimide), an appropriate catalyst (e.g. 4 dimethylaminopyridine) and a reaction-inert organic solvent (e.g. THF);

(h) for compounds of formula I in which D represents —(CH$_2$)$_n$NH$_2$, reduction of a corresponding compound of formula IX,

IX

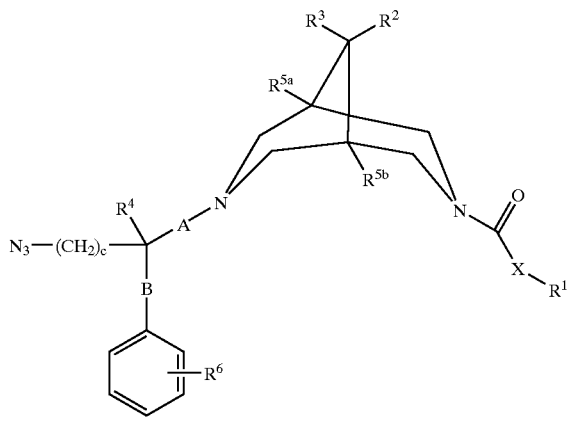

wherein c, $R^1$, $R^2$, $R^3$, $R^4$, $R^{5a}$, $R^{5b}$, $R^6$, A, B and X are as hereinbefore defined, for example by hydrogenation at a suitable pressure in the presence of a suitable catalyst (e.g. palladium on carbon) and an appropriate solvent (e.g. a water-ethanol mixture);

(i) for compounds of formula I in which D represents —N($R^{11}$)C(O)NH($R^{15}$), in which $R^{11}$ and $R^{15}$ are as hereinbefore defined, except that $R^{11}$ does not represent C(O)$R^{18}$, reaction of a corresponding compound of formula I in which D represents —N($R^{11}$)H, in which $R^{11}$ is as hereinbefore defined except that is does not represent C(O)$R^{18}$ in which $R^{18}$ is as hereinbefore defined, with a compound of formula X, $$R^{15}N=C=O \qquad X$$

wherein $R^{15}$ is as hereinbefore defined, for example at ambient temperature (e.g. 25° C.) in the presence of a suitable solvent (e.g. benzene);

(j) for compounds of formula I in which D represents —N(H)[C(O)]$_2$NH$_2$, reaction of a corresponding compound of formula I in which D represents —NH$_2$ with oxalic acid diamide, for example at between −10 and 25° C. in the presence of a suitable coupling agent (e.g. 1-(3-dimethylamino-propyl)-3-ethylcarbodiimide), an appropriate activating agent (e.g. 1-hydroxybenzotriazole), a suitable base (e.g. triethylamine) and a reaction-inert organic solvent (e.g. DMF);

(k) for compounds of formula I in which D represents —N($R^{11}$)C(O)$R^{16}$, in which $R^{11}$ and $R^{16}$ are as hereinbefore defined, except that $R^{11}$ does not represent C(O)$R^{18}$, reaction of a corresponding compound of formula I in which D represents —N($R^{11}$)H, in which $R^{11}$ is as hereinbefore defined except that it does not represent C(O)$R^{18}$, with a compound of formula XI, $$R^{16}C(O)R^x \qquad XI$$

wherein $R^x$ represents a suitable leaving group, such as $C_{1-4}$ alkoxy, Hal (e.g. Cl, Br) or p-nitrophenyl and $R^{16}$ is as hereinbefore defined, for example at between ambient and reflux temperature in the presence of a suitable solvent (e.g. methanol or DMSO) and (as appropriate) a suitable base (e.g. $K_2CO_3$ or TEA);

(l) for compounds of formula I in which D represents —N(H)$R^{10}$ and $R^{10}$ is as hereinbefore defined except that it does not represent H or —C(NH)NH$_2$, reaction of a corresponding compound of formula I wherein D represents —NH$_2$ with a compound of formula XIA, $$R^{10a}L^1 \qquad XIA$$

wherein $R^{10a}$ represents $R^{10}$ as hereinbefore defined, except that it does not represent H or —C(NH)NH$_2$ and $L^1$ is as hereinbefore defined, for example under conditions that are known to those skilled in the art;

(m) for compounds of formula I which are bispidine-nitrogen N-oxide derivatives, oxidation of the corresponding bispidine nitrogen of a corresponding compound of formula I, in the presence of a suitable oxidising agent (e.g. m-chloroperbenzoic acid), for example at 0° C. in the presence of a suitable organic solvent (e.g. DCM);

(n) for compounds of formula I which are $C_{1-4}$ alkyl quaternary ammonium salt derivatives, in which the alkyl group is attached to a bispidine nitrogen, reaction, at the bispidine nitrogen, of a corresponding compound of formula I with a compound of formula XII, $$R^aHal \qquad XII$$

wherein $R^1$ represents $C_{1-4}$ alkyl and Hal is as hereinbefore defined, for example at room temperature in the presence of an appropriate organic solvent (e.g. DMF), followed by purification (using e.g. HPLC) in the presence of a suitable counter-ion provider (e.g. NH$_4$OAc);

(o) for compounds of formula I in which D and $R^4$ both represent H, A represents $C_{1-6}$ alkylene, B represents —N($R^{24}$)(CH$_2$)$_m$— and m and $R^{24}$ are as hereinbefore defined, reaction of a compound of formula XIII,

XIII

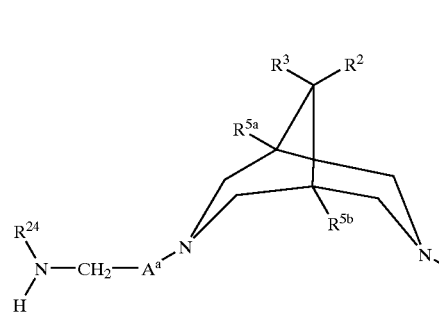

wherein $A^a$ represents $C_{1-6}$ alkylene and $R^1$, $R^2$, $R^3$, $R^{5a}$, $R^{5b}$, $R^{24}$ and X are as hereinbefore defined with a compound of formula XIV,

XIV

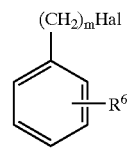

wherein $R^6$, m and Hal are as hereinbefore defined, for example at 40° C. in the presence of a suitable organic solvent (e.g. acetonitrile);

(p) reaction of a compound of formula II, as hereinbefore defined, with a compound of formula XV, $$R^1XH \qquad XV$$

wherein $R^1$ and X are as hereinbefore defined, in the presence of 1,1'-carbonyldiimidazole, for example by refluxing in the presence of a suitable organic solvent (e.g. THF);

(q) for compounds of formula I in which one of $R^2$ and $R^3$ represents —$NH_2$ and the other represents H, reduction of a compound of formula XVA,

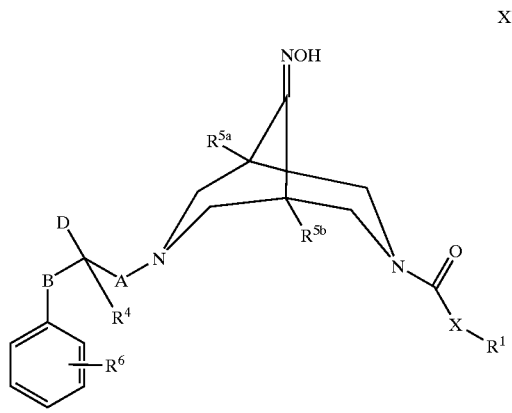

XVA wherein $R^1$, $R^4$, $R^{5a}$, $R^{5b}$, $R^6$, A, B, D and X are as hereinbefore defined, in the presence of a suitable reducing agent (e.g. $LiAlH_4$), for example under conditions that are well known to those skilled in the art;

(r) for compounds of formula I in which one or both of $R^2$ and $R^3$ represent —$N(R^{7a})R^{7b}$ in which one or both or $R^{7a}$ and $R^{7b}$ represents $C_{1-4}$ alkyl, alkylation of a corresponding compound of formula I in which $R^2$ and/or $R^3$ represent —$N(R^{7a})R^{7b}$ (as appropriate) in which $R^{7a}$ and/or $R^{7b}$ (as appropriate) represent H, using a compound of formula XVB, $R^{7c}L^1$   XVB wherein $R^{7c}$ represents $C_{1-6}$ alkyl and $L^1$ is as hereinbefore defined, for example under conditions that are well known to those skilled in the art; or (s) conversion of one $R^6$ substituent to another using techniques well known to those skilled in the art.

Compounds of formula II may be prepared by reaction of a compound of formula XVI,

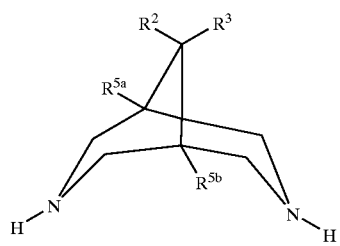

XVI wherein $R^2$, $R^3$, $R^{5a}$ and $R^{5b}$ are as hereinbefore defined, with a compound of formula VI as hereinbefore defined, for example as described hereinbefore for synthesis of compounds of formula I (process step (c)), or, in the case of compounds of formula II wherein A represents $CH_2$ and D represents OH or $N(R^{10})H$, with a compound of formula V, for example as described hereinbefore for synthesis of compounds of formula I (process step (b)).

Compounds of formula II in which $R^2$ and $R^3$ both represent H may be prepared by reduction of a compound of formula XVII,

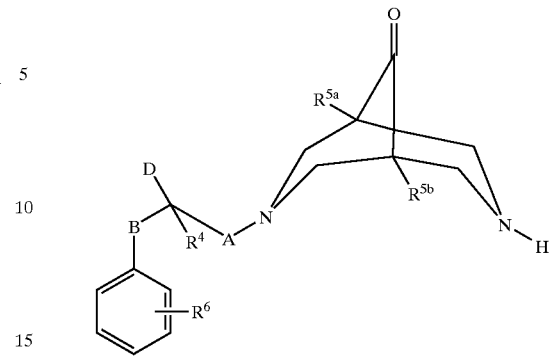

XVII wherein $R^4$, $R^{5a}$, $R^{5b}$, R $R^6$, A, B and D are as hereinbefore defined, and in which the C=O group may be activated using an appropriate agent, such as tosylhydrazine, for example as described hereinbefore for synthesis of compounds of formula I (process step (e)).

Compounds of formula II in which $R^2$ represents OH and $R^3$ represents optionally substituted $C_{1-4}$ alkyl, may be prepared by reaction of a compound of formula XVII, or a protected derivative thereof, with a compound of formula XVIIA $R^{3'}MgHal$   XVIIA wherein $R^{3'}$ represents $C_{1-4}$ alkyl (optionally substituted and/or terminated with one or more cyano groups) and Hal is as hereinbefore defined, for example at between −25° C. and ambient temperature in the presence of a suitable solvent (e.g. diethyl ether).

Compounds of formula IV may be prepared by reaction of a compound of formula XVI, as hereinbefore defined, with a compound of formula III as hereinbefore defined, for example as described hereinbefore for synthesis of compounds of formula I (process step (a)).

Compounds of formula IV may alternatively be prepared by reaction of a compound of formula XVI, as hereinbefore defined, with a compound of formula XV, as hereinbefore defined, in the presence of 1,1'-carbonyldiimidazole, for example as described hereinbefore for synthesis of compounds of formula I (process step (p)).

Compounds of formula IV in which $R^2$ and $R^3$ represent H may alternatively be prepared by reduction of a corresponding compound of formula XVIII,

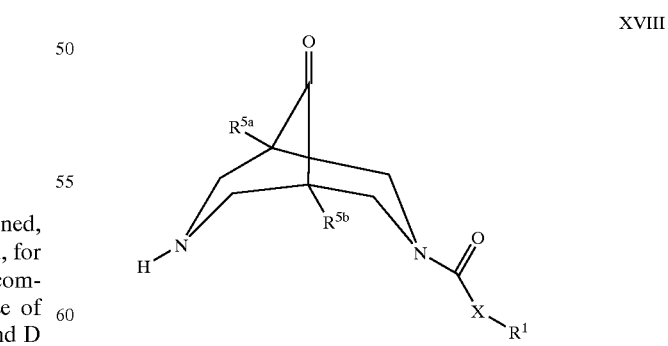

XVIII wherein $R^1$, $R^{5a}$, $R^{5b}$ and X are as hereinbefore defined, and in which the bridgehead C=O group may be activated using an appropriate agent, such as tosylhydrazine, for example as described hereinbefore for compounds of formula I (process step (e)).

Compounds of formula V may be prepared in accordance with techniques which are well known to those skilled in the art. For example, compounds of formula V in which:

(1) B represents —CH$_2$O— and Y represents O may be prepared by reaction of a compound of formula XIX,

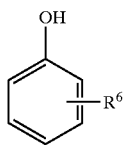

XIX wherein R$^6$ is as hereinbefore defined, with a compound of formula XX,

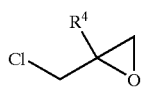

XX wherein R$^4$ is as hereinbefore defined, for example at elevated temperature (e.g. between 60° C. and reflux temperature) in the presence of a suitable base (e.g. K$_2$CO$_3$ or NaOH) and an appropriate organic solvent (e.g. acetonitrile or toluene/water), or as otherwise described in the prior art;

(2) B represents —CH$_2$O— and Y represents O may alternatively be prepared by reaction of a compound of formula XIX, as hereinbefore defined, with a compound of formula XXI,

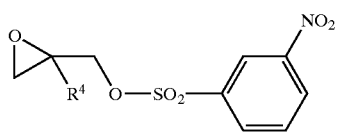

XXI wherein R$^4$ is as hereinbefore defined, for example between room temperature and elevated temperature (e.g. 40° C.) in the presence of a suitable base (e.g. K$_2$CO$_3$ or potassium ethoxide) and an appropriate organic solvent (e.g. acetonitrile or DMF);

(3) B represents a single bond, Y represents O and R$^4$ represents H may be prepared by reduction of a compound of formula XXII,

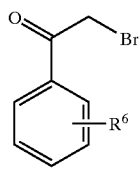

XXII wherein R$^6$ is as hereinbefore defined, for example at between −15° C. and room temperature in the presence of a suitable reducing agent (e.g. NaBH$_4$) and an appropriate organic solvent (e.g. THF), followed by an internal displacement reaction of the resultant intermediate, for example at room temperature in the presence of a suitable base (e.g. K$_2$CO$_3$) and an appropriate organic solvent (e.g. acetonitrile);

(4) B represents C$_{1-4}$ alkylene, —(CH$_2$)$_m$N(R$^{24}$)—, —(CH$_2$)$_n$ S(O)$_2$— or —(CH$_2$)$_m$O— (in which latter three groups m represents 1, 2, 3 or 4) and Y represents O may be prepared by oxidation of a compound of formula XXIII,

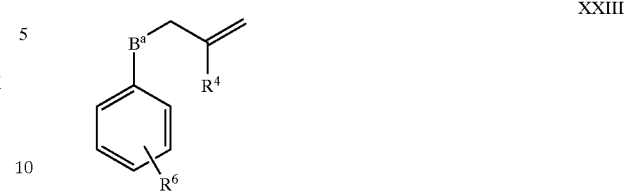

XXIII in which B$^a$ represents a single bond, C$_{1-3}$ alkylene, —(CH$_2$)$_m$N(R$^{24}$), —(CH$_2$)$_{m-1}$S(O)$_2$— or —(CH$_2$)$_{m-1}$O— (in which latter three groups m represents 1, 2, 3 or 4) and R$^{24}$ and R$^6$ are as hereinbefore defined, in the presence of a suitable oxidising agent (e.g. m-chloroperbenzoic acid), for example by refluxing in the presence of a suitable organic solvent (e.g. dichloromethane); or (5) B represents —(CH$_2$)$_m$O—, Y represents N(R$^{10}$) and R$^{10}$ represents —S(O)$_2$R$^{13}$ or —C(O)OR$^{17}$ may be prepared by cyclisation of a compound of formula XXIIIA,

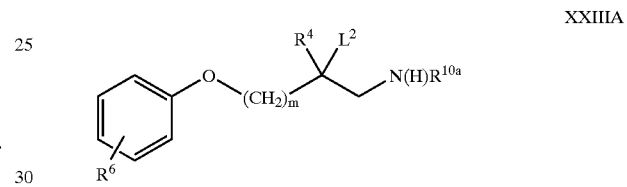

XXIIIA wherein R$^{10a}$ represents —S(O)$_2$R$^{13}$ or —C(O)OR$^{17}$ and m, R$^4$, R$^6$, R$^{13}$, R$^{17}$ and L$^2$ are as hereinbefore defined, for example at between 0° C. and reflux temperature in the presence of a suitable base (e.g. sodium hydroxide), an appropriate solvent (e.g. dichloromethane, water, or a mixture thereof) and, if necessary, a phase transfer catalyst (such as tetrabutylammonium hydrogensulfate).

Compounds of formula VI may be prepared by standard techniques. For example compounds of formula VI in which:

(1) B represents —(CH$_2$)$_m$O— may be prepared by coupling a compound of formula XIX, as hereinbefore defined, to a compound of formula XXIV,

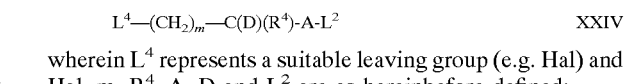

L$^4$—(CH$_2$)$_m$—C(D)(R$^4$)-A-L$^2$    XXIV wherein L$^4$ represents a suitable leaving group (e.g. Hal) and Hal, m, R$^4$, A, D and L$^2$ are as hereinbefore defined;

(2) B represents —C(O)N(R$^{24}$)— may be prepared by coupling a compound of formula XXV,

XXV wherein R$^6$ and R$^{24}$ are as hereinbefore defined, to a compound of formula XXVI,

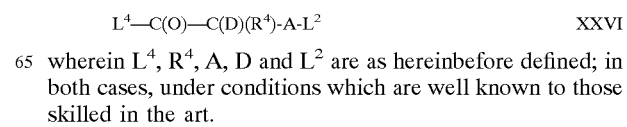

L$^4$—C(O)—C(D)(R$^4$)-A-L$^2$    XXVI wherein L$^4$, R$^4$, A, D and L$^2$ are as hereinbefore defined; in both cases, under conditions which are well known to those skilled in the art.

Compounds of formulae V and VI in which B represents —(CH$_2$)$_m$S(O)— or —(CH$_2$)$_m$S(O)$_2$— may be prepared by oxidation of the corresponding compounds of formulae V and VI (respectively) wherein B represents —(CH$_2$)$_m$S—, wherein m is as hereinbefore defined, in the presence of an appropriate amount of a suitable oxidising agent (e.g. m-chloroperbenzoic acid) and an appropriate organic solvent.

Compounds of formula VII may be prepared in a similar fashion to compounds of formula I (see, for example, process steps (a), (b) or (c)).

Alternatively, compounds of formula VII in which A represents C$_2$ alkylene may be prepared by reaction of a corresponding compound of formula IV, as hereinbefore defined with a compound of formula XXVII,

XXVII

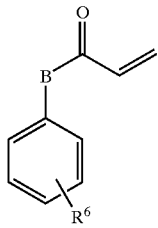

wherein R$^6$ and B are as hereinbefore defined, for example a room temperature in the presence of a suitable organic solvent (e.g. ethanol).

Compounds of formula IX may be prepared by reaction of a corresponding compound of formula XXVIIA,

XXVIIA

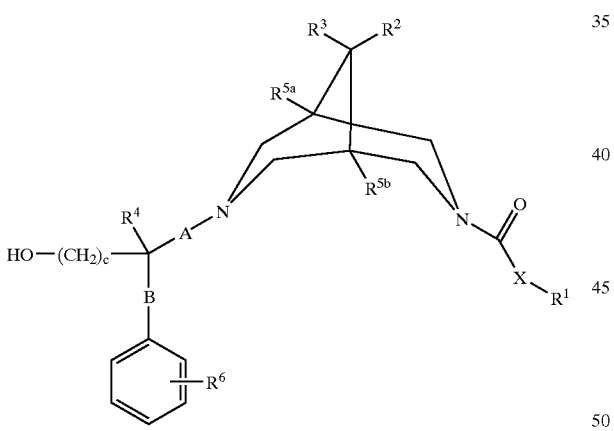

wherein c, R$^1$, R$^2$, R$^3$, R$^4$, R$^{5a}$, R$^{5b}$, R$^6$, X, A and B are as hereinbefore defined with a compound of formula XXVIIB, R$^y$S(O)$_2$Cl    XXVIIB wherein R$^y$ is C$_{1-4}$ alkyl or aryl (which two groups are optionally substituted with one or more substituents selected from C$_{1-4}$ alkyl or halo), for example at between –10 and 25° C. in the presence of a suitable solvent (e.g. dichloromethane), followed by reaction with a suitable source of the azide ion (e.g. sodium azide) for example at between ambient and reflux temperature in the presence of an appropriate solvent (e.g. DMF) and a suitable base (e.g. NaHCO$_3$).

Compounds of formula IX may alternatively be prepared by reaction of a compound of formula IV as hereinbefore defined with a compound of formula XXVIIC,

XXVIIC

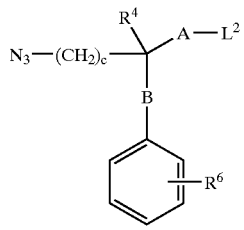

wherein L$^2$, R$^4$, R$^6$, A, B and c are as hereinbefore defined, for example under analogous conditions to those described hereinbefore for preparation of compounds of formula I (process step (c)).

Compounds of formula XIII may be prepared by removing an optionally substituted benzyloxycarbonyl unit from (i.e. deprotecting) a corresponding compound of formula I in which D and R$^4$ both represent H and B represents —N(R$^{24}$)C(O)O(CH$_2$)—, A represents A$^a$ and A$^a$ is as hereinbefore defined under conditions which are well known to those skilled in the art.

Compounds of formula XVA may be prepared by reaction of a corresponding compound of formula VIII with hydroxylamine, for example at elevated temperature (e.g. at reflux) in the presence of a suitable organic solvent (e.g. methanol).

Compounds of formula XVI in which R$^2$ and R$^3$ both represent H may be prepared by reduction of a compound of formula XXVIII,

XXVIII

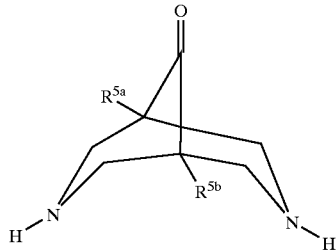

wherein R$^{5a}$ and R$^{5b}$ are as hereinbefore defined, under appropriate conditions (for example conditions such as those described in respect of the preparation of compounds of formula I (process step (e))).

Compounds of formula XVI in which R$^2$ represents OH and R$^3$ represents R$^{3a}$ may be prepared by reaction of a corresponding compound of formula XXVIII as hereinbefore defined, with a compound of formula XVIIA as hereinbefore defined, under appropriate conditions (for example conditions such as those described for the production of compounds of formula II in which R$^2$ represents OH and R$^3$ represents R$^3$).

Compounds of formula XVI in which R$^2$ and R$^3$ together represent —O—(CH$_2$)-O—, —(CH$_2$)$_3$—, —(CH$_2$)$_4$— or —(CH$_2$)$_5$— may be prepared by reduction of a compound of formula XXVIIIA

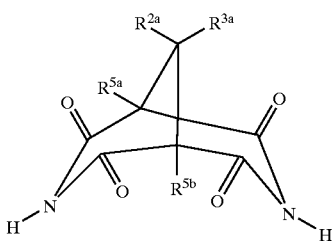

wherein $R^{2a}$ and $R^{3a}$ together represent —O—$(CH_2)_2$—O—, —$(CH_2)_3$—, —$(CH_2)_4$— or —$(CH_2)_5$— and $R^{5a}$ and $R^{5b}$ are as hereinbefore defined in the presence of a suitable reducing agent (e.g. LiAlH$_4$) under conditions that are well known to those skilled in the art.

Compounds of formula XXVIIA may be prepared in analogous fashion to corresponding compounds of formula I.

Compounds of formula XXVIIC may be prepared in analogous fashion to a compound of formula IX (i.e. from the corresponding alcohol including a —$(CH_2)_n$OH group).

Compounds of formulae VIII, XVII, XVIII and XXVm may be prepared, advantageously, by reaction of a compound of formula XXIX,

XXIX

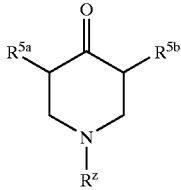

wherein $R^z$ represents H or —C(O)XR$^1$ and R$^1$, $R^{5a}$, $R^{5b}$ and X are as hereinbefore defined with (as appropriate) either (1) a compound of formula XXX,

XXX

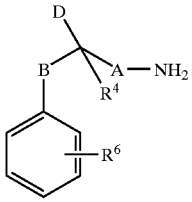

or a protected derivative thereof, wherein $R^4$, $R^6$, A, B and D are as hereinbefore defined, or (2) NH$_3$ (or a protected (e.g. benzyl) derivative thereof), in all cases in the presence of a formaldehyde (i.e. an appropriate source of formaldehyde, such as paraformaldehyde or formalin solution).

The formation of compounds of formulae VII, XVII, XVIII and XXVIII may be carried out in this way for example at between room temperature and reflux (depending upon the concentration of the reactants) in the presence of an appropriate solvent (e.g. ethanol or methanol) and, preferably, in the presence of an organic acid (e.g. a C$_{1-4}$ carboxylic acid, especially acetic acid).

Compounds of formula XXVIIIA may be prepared in accordance with techniques which are well known to those skilled in the art. For example, compounds of formula XXVIIIA in which R$^1$ and R$^3$, together represent —(CH$_2$)$_3$—, —(CH$_2$)$_4$— or —(CH$_2$)$_5$— and $R^{5a}$ and $R^{5b}$ represent H may be prepared by reaction of a compound of formula XXXI,

XXXI

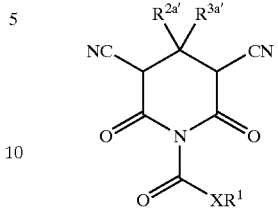

wherein $R^{2a}$ and R$^3$, together represent —(CH$_2$)$_3$—, —(CH$_2$)$_4$— or —(CH$_2$)$_n$— and X and R$^1$ are as hereinbefore defined with a mixture of phosphoric acid and sulfuric acid, for example at 120° C.

Compounds of formula XXX are well known in the literature or are readily available using known techniques. For example, compounds of formula XXX wherein D represents —OH, R$^4$ represents H and A represents CH$_2$ may be prepared by reaction of a compound of formula V in which R$^4$ represents H with ammonium hydroxide under conditions which are well known to those skilled in the art.

Compounds of formulae III, VIIIA, X, XI, XIA, XII, XIV, XV, XVB, XVIIA, XIX, XX, XXI, XXII, XXIII, XXIIIA, XXIV, XXV, XXVI, XXVII, XXVIIB, XXIX and XXXI, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other substituents using techniques well known to those skilled in the art. For example, nitrobenzene may be reduced to an aminobenzene, hydroxy may be converted to alkoxy, alkoxy may be hydrolysed to hydroxy etc.

The compounds of the invention may be isolated from their reaction mixtures using conventional techniques.

It will be appreciated by those skilled in the art that, in the processes described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyloxy groups (e.g. methyl- and ethylcarbonyloxy groups). Suitable protecting groups for amino include benzyl, tert-butyloxycarbonyl, 9-fluorenylmethoxycarbonyl or benzyloxycarbonyl. Suitable protecting groups for carboxylic acid include C$_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided compounds of formulae II, VIII and XVII as hereinbefore defined, or protected derivatives of all of these compounds, provided that, in all cases, when $R^{5a}$ and $R^{5b}$ both represent H, then D does not represent H or OH. There is further provided a compound of formula IV as hereinbefore defined, or a protected derivative thereof, provided that when $R^{5a}$ and $R^{5b}$ both represent H, then at least one of $R^2$ and $R^3$ represents $OR^7$, $OC(O)R^8$ or $C_{1-4}$ alkyl, which alkyl group is substituted and/or terminated with one or more nitro or cyano groups.

Medical and Pharmaceutical Use

The compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization, thus prolonging the QT interval, and, in particular, to exhibit class II activity. Although compounds of the invention have been found to exhibit class III activity in particular, in the treatment of arrhythmias, their mode(s) of activity is/are not necessarily restricted to this class.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base, a pharmaceutically acceptable ion exchanger or a non-toxic organic or inorganic acid addition salt, in a pharmaceutically acceptable dosage form.

Depending upon the disorder and patient to be treated, as well as the route of administration, the compositions may be administered at varying doses.

The compounds of the invention may also be combined with any other drugs useful in the treatment of arrhythmias and/or other cardiovascular disorders.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.05 to 5.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I, class II and/or class IV activity in addition to class III activity)) than, be more potent than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects in Anaesthetised Guinea Pigs

Guinea pigs weighing between 660 an 1100 g were used. The animals were housed for at least one week before the experiment and had free access to food and tap water during that period.

Anaesthesia was induced by an intraperitoneal injection of pentobarbital (40 to 50 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (2 ms duration, twice the diastolic threshold) was performed with a custom-made constant current stimulator. The heart was paced at a frequency just above the normal sinus rate during 1 minute every fifth minute throughout the study.

The blood pressure, the MAP signal and the lead II ECG were recorded on a Mingograph ink-jet recorder (Siemens-Elema, Sweden). All signals were collected (sampling frequency 1000 Hz) on a PC during the last 10 seconds of each pacing sequence and the last 10 seconds of the following minute of sinus rhythm. The signals were processed using a custom-made program developed for acquisition and analysis of physiological signals measured in experimental animals (see Axenborg and Hirsch, Comput. Methods Programs Biomed. 41, 55 (1993)).

The test procedure consisted of taking two basal control recordings, 5 minutes apart, during both pacing and sinus rhythm. After the second control recording, the first dose of the test substance was infused in a volume of 0.2 mL into the jugular vein catheter for 30 seconds. Three minutes later, pacing was started and a new recording was made. Five minutes after the previous dose, the next dose of test substance was administered. Six to ten consecutive doses were given during each experiment.

Data Analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynanmic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by 10% from the baseline was used as an index to assess the class m electrophysiological potency of the agent under investigation ($D_{10}$).

The invention is illustrated by way of the following examples.

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS), a Hewlett Packard model 6890 gas chromatograph connected to a Hewlett-Packard model 5973A mass spectrometer via a Hewlett Packard HP-5-MS GC column, or a Shimadzu QP-5000 GC/mass spectrometer (CI, methane).

$^1$H NMR and $^{13}$C NMR measurements were performed on a BRUKER ACP 300 and Varian UNITY plus 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C NMR measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

Example 1

Ethyl 7-[3-(4-cyanophenoxy)-2-hydroxypropyl]-9-hydroxy-3,7-diazabicyclo[3.3.1]nonane-3-carboxylate; diastereoisomers 1

(i) 4-(2-Oxiranylmethoxy)benzonitrile)

Epichlorohydrin (800 mL) and $K_2CO_3$ (414 g) were added to a stirred solution of p-cyanophenol (238 g) in 2.0 L of acetonitrile. The reaction mixture was brought to reflux under an inert atmosphere for 2 h before being filtered whilst still hot. The resulting filtrate was concentrated to give a clear oil. This was crystallized from di-iso-propyl ether to give the sub-title compound in a 75% yield.

(ii) 3-(4-Cyanophenoxy)-2-hydroxypropylamine

IPA (300 mL) was added to a stirred suspension of 4-(2-oxiranylmethoxy)benzonitrile (from step (i) above; 100 g; 571 mmol) in $NH_3$ (500 mL; conc.), and the reaction mixture was stirred at rt for 3 days. The precipitate was filtered off and the residue concentrated and recrystallized from MeCN to give the sub-title compound in a 46% yield.

(iii) Ethyl 7-[3-(4-cyanophenoxy)-2-hydroxypropyl]-9-oxy-3,7-diazabicyclo[3.3.1] nonane-3-carboxylate Glacial acetic acid (0.30 g; 5.0 mmol) in methanol (5 mL), and then paraformaldehyde (0.33 g; 11.0 mmol), were added to a stirred methanolic (5 mL) suspension of 3-(4-cyanophenoxy)-2-hydroxypropylamine (from step (ii) above; 0.96 g; 5.0 mmol) under an inert atmosphere ($N_2$). The temperature was brought to 55° C. and a solution of 1-ethoxycarbonyl-4-piperidone (0.86 g; 5.0 mmol) in MeOH (5 mL) was added and the reaction mixture stirred for 6 h. The solids were filtered off and the solution was concentrated. The solid residue was partitioned between water and diethyl ether. The aqueous phase was collected and the pH adjusted to 10 (4 M NaOH) and extracted with $CH_2Cl_2$. The combined organic layers were concentrated and purified using column chromatography ($CH_2Cl_2$:MeOH; 19:1) to give the sub-tide compound in 30% yield.

$^{13}$C NMR in $CDCl_3$: δ 14.5, 48.0, 50.6, 57.3, 61.2, 62.2, 65.4, 70.3, 104.2, 115.3, 119.0, 133.9, 157.9, 161.9, 211.7.

(iv) Ethyl 7-[3-(4-cyanophenoxy)-2-hydroxypropyl]-9-hydroxy-3,7-diazabicyclo[3.3.1] nonane-3-carboxylate; diastereoisomers 1

Sodium borohydride (100 mg; 2.6 mmol) was added to a cooled (0° C.), stirred solution of ethyl 7-[3-(4-cyanophenoxy)-2-hydroxypropyl]-9-oxy-3,7-diazabicyclo [3.3.1]nonane-3-carboxylate (from step (iii) above; 354 mg; 0.91 mmol) in MeOH (3 mL). The reaction mixture was then stirred at rt for 1 h. The solvent was evaporated and the residue partitioned between $CH_2Cl_2$ and $NaHCO_3$ (aq.). The organic layer was separated, dried, concentrated and subjected to column chromatography (hexane:EtOAc:MeOH; 35:60:5) to give two separable diastereoisomeric pairs. The title compound refers to the less polar diastereoisomers and was isolated in 58% yield.

$^{13}$C NMR in $CDCl_3$: δ 15.0, 37.0, 48.9, 54.2, 61.5, 63.3, 66.1, 69.2, 72.1, 84.0, 104.5, 11 6.4, 119.6, 134.7, 161.9, 163.4.

Example 2

Ethyl 7-[3-(4-cyanophenoxy)-2-hydroxypropyl]-9-hydroxy-3,7-diazabicyclo[3.3.1]nonane-3-carboxylate; diastereoisomers 2

The title compound was isolated in 24% yield as the more polar diastereoisomers from Example 1 above.

Example 3 tert-Butyl 7-[3-(4-cyanophenoxy)-2-hydroxypropyl]-9-hydroxy-3,7-diazabicyclo[3.3.1]nonane-3-carboxylate; diastereoisomers 1

(i) tert-Butyl 7-[3-(4-cyanophenoxy)-2-hydroxypropyl]-9-oxy-3,7-diazabicyclo[3.3.1]nonane-3-carboxylate The sub-title compound was prepared according to the procedure described in Example 1(iii) above using 1-tert-butoxycarbonyl-4-piperidone in place of 1-ethoxycarbonyl-4-piperidone.

CI-MS (methane): m/z=416 (MH$^+$).

(ii) tert-Butyl 7-[3-(4-cyanophenoxy)-2-hydroxypropyl]-9-hydroxy-3,7-diazabicyclo[3.3.1]nonane-3-carboxylate; diastereoisomers 1

The sub-title compound was prepared according to the procedure described in Example 1(iv) above, using tert-butyl 7-[3-(4-cyanophenoxy)-2-hydroxypropyl]-9-oxy-3,7-diazabicyclo[3.3.1]-nonane-3-carboxylate (from step (i) above) in place of ethyl 7-[3-(4-cyanophenoxy)-2-hydroxypropyl]-9-oxy-3,7-diazabicyclo[3.3.1]-nonane-3-carboxylate. Spectral data was in agreement with data obtained from diastereoisomers 2 (described in Example 4). The title compound refers to the less polar diastereoisomers.

Example 4 tert-Butyl 7-[3-(4cyanophenoxy)-2-hydroxypropyl]-9-hydroxy-3,7-diazabicyclo[3.3.1]nonane-3-carboxylate; diastereoisomers 2

The title compound was isolated as the more polar diastereoisomers from Example 3 above. $^{13}$C NMR in $CDCl_3$; δ 28.6, 35.5, 47.4, 53.5, 61.4, 65.1, 69.2, 70.7, 79.9, 103.9, 115.3, 119.2, 133.9, 156.0, 162.2.

Example 5 tert-Butyl 7-[(2S)-3-(4-cyanophenoxy)-2-hydroxypropyl]-9-hydroxy-9-methyl-3,7-diazabicyclo[3.3.1]nonane-3-carboxylate (i) 3,7-Dibenzyl-3,7-diazabicyclo[3.3.1]nonane-9-one The sub-title compound was prepared according to the procedure described in J. Org. Chem., 41(9), 1976, pp. 1593-1597.

(ii) 3,7-Dibenzyl-9-hydroxy-9-methyl-3,7-diazabicyclo[3.3.1]nonane

A solution of 3,7-dibenzyl-3,7-diazabicyclo[3.3.1]nonane-9-one (from step (i) above; 2.05 g; 6.4 mmol) in diethyl ether (15 mL) was added to a stirred solution of methyl magnesium chloride (12.8 mmol) in diethyl ether (8 mL) over 80 minutes. The reaction mixture was subsequently stirred for 20 minutes and then quenched with HCl (1 M). The aqueous layer was separated, concentrated and partitioned between EtOAc and NaOH (2 M). The organic layer was separated and subsequently treated with ion exchange resin (Amberlyst IRA 400), the solvent removed and the residue subjected to column chromatography (hexane:EtOAc; 1:1 with $NH_3$ sat. MeOH; gradient 0-32%) to give the sub-title compound as a diastereoisomeric mixture in a 60% yield.

(iii) tert-Butyl 7-benzyl-9-hydroxy-9-methyl-3,7-diazabicyclo[3.3.1]-nonane-3-carboxylate A solution of 3,7-dibenzyl-9-hydroxy-9-methyl-3,7-diazabicyclo[3.3.1]-nonane (from step (ii) above, 1.0 g, 4.0 mmol) and di-tert-butyl dicarbonate (0.98 g, 4.25 mmol) in EtOH (50 mL) was hydrogenated over Pd/C for 20 minutes, filtered through a pad of Celite® and concentrated. Purification by column chromatography gave the sub-title compound in a 40% yield.

(iv) tert-Butyl 9-hydroxy-9-methyl-3,7-diazabicyclo[3.3.1]nonane-3-carboxylate

A solution of tert-butyl 7-benzyl-9-hydroxy-9-methyl-3,7-diazabicyclo-[3.3.1]nonane-3-carboxylate (from step (iii) above; 450 mg, 1.3 mmol) in aqueous ethanol (50 mL of 95%) was hydrogenated over 5% Pd/C at 1 atm until tlc indicated that the reaction was complete. The catalyst was removed by filtration through a pad of Celite®, and the filtrate concentrated under reduced pressure to give the sub-title compound in quantitative yield.

(v) 4-[(2S)-Oxiranylmethoxy]benzonitrile

The subtitle compound was prepared in 90% yield according to the procedure described in Example 1(i) above, but using (R)-(−)-epichlorohydrin.

$^{13}$C NMR in $CDCl_3$: δ 44.4, 49.7, 69.0, 104.6, 115.3, 119.0, 134.0, 161.6.

(vi) tert-Butyl 7-[(2S)-3-(4-cyanophenoxy)-2-hydroxypropyl]-9-hydroxy-9-methyl-3,7-diazabicyclo[3.3.1]nonane-3-carboxylate 4-[(2S)-Oxiranylmethoxy]benzonitrile (from step (v) above, 247 mg, 1.4 mmol) was added to a stirred solution of tert-butyl 9-hydroxy-9-methyl-3,7-diazabicyclo[3.3.1] nonane-3-carboxylate (from step (iv) above, 328 mg, 1.28 mmol) in acetonitrile:water (4:1). The reaction was heated to 60° C. for 12 h, after which stirring was continued at rt for a further 48 h.

The reaction mixture was concentrated, dissolved in $CH_2Cl_2$, dried ($MgSO_4$) and then concentrated again. The residue was purified using column chromatography to give the title compound in 44% yield.

$^{13}$C NMR in $CDCl_3$: δ 14.10, 21.21, 21.79, 22.81, 25.95, 26.05, 28.44, 28.86, 31.75, 39.62, 39.99, 40.13, 40.31, 43.99, 46.45, 47.65, 52.21, 54.09, 55.71, 57.82, 60.02, 60.32, 60.55, 65.24, 67.95, 68.42, 68.65, 70.54, 79.43, 79.74, 103.82, 108.03, 115.30, 119.11, 126.22, 129.47, 133.81, 133.92, 139.48, 143.11, 156.05, 156.12, 156.19, 156.33, 162.09

Example 6 tert-Butyl 7-[3-(4-cyanophenoxy)-2-hydroxypropyl]-9-benzoyloxy-3,7-diazabicyclo[3.3.1]nonane-3-carboxylate (i) tert-Butyl 7-[3-(4-cyanophenoxy)-2-(tert-butyldimethylsilyloxypropyl)]-9-oxy-3,7-diazabicyclo[3.3.1]nonane-3-carboxylate A mixture of tert-butyldimethylchlorosilane (5.39 g, 35.7 mmol), tert-butyl 7-[3-(4-cyanophenoxy)-2-hydroxypropyl]-9-oxy-3,7-diazabicyclo-[3.3.1]nonane-3-carboxylate (from Example 3(i) above; 13.5 g; 32.5 mmol) and imidazole (4.86 g; 71.4 μmmol) in DMF was stirred for 20 h at rt. The mixture was diluted with $CH_2Cl_2$ (200 mL), then washed with water (2×100 mL) and saturated brine (2×100 mL). The organic layer was separated, dried ($Na_2SO_4$) and then concentrated to give a yellow oil. This was purified by column chromatography (EtOAc) to give the sub-title compound in 77% yield.

(ii) tert-Butyl 7-[3-(4-cyanophenoxy)-2-(tert-butyldimethylsilyloxy-propyl)]-9-hydroxy-3,7-diazabicyclo[3.3.1]-nonane-3-carboxylate Sodium borohydride (2.66 g; 70.2 mmol) was added in portions to a cooled (0° C.), stirred solution of tert-butyl 7-[3-(4-cyanophenoxy)-2-(tert-butyldimethylsilyloxypropyl)]-9-oxy-3,7-diazabicyclo[3.3.1]nonane-3-carboxylate (from step (i) above; 13.3 g; 25.1 mmol) in methanol (75 mL). The mixture was stirred for 3 h at rt before the solvent was evaporated under reduced pressure. The oily residue was diluted with 100 mL of saturated aqueous $NaHCO_3$, and then extracted with $CH_2Cl_2$ (3×100 mL). The combined organic layers were dried ($Na_2SO_4$) and then concentrated to give a white foam. This was purified by column chromatography (EtAc:hexane; 1:1) to give the sub-title compound in 50% yield.
CI-MS (methane): m/z 532 ($MH^+$).
$^{13}C$ NMR in $CDCl_3$: δ −4.7, 4.5, 25.7, 28.6, 35.4, 35.6, 41.7, 42.6, 47.7, 48.6, 53.0, 53.8, 60.3, 61.5, 61.9, 68.9, 69.9, 71.5, 78.9, 79.5, 103.6, 103.9, 115.6, 119.3, 133.9, 155.2, 162.3

(iii) tert-Butyl 7-[3-(4-cyanophenoxy)-2-(tert-butyldimethylsilyloxy-propyl)]-9-benzoyloxy-3,7-diazabicyclo[3.3.1]nonane-3-carboxylate Benzoic acid (517 mg; 4.23 mmol), 1-(3-dimethylaminopropyl)-3-ethylcarbodiimide hydrochloride (811 mg; 4.23 mmol) and 4-dimethylaminopyridine (35 mg; 0.282 mmol) were added to tert-butyl 7-[3-(4-cyanophenoxy)-2-(tert-butyldimethylsilyloxypropyl)]-9-hydroxy-3,7-diazabicyclo[3.3.1]nonane-3-carboxylate (from step (ii) above; 1.5 g; 2.82 mmol) in 15 mL of THF. The mixture was stirred for 24 h at rt before being diluted with ethyl acetate. The resulting solution was washed with water (2×50 mL) and brine (2×50 mL). The organic layer was then separated, dried ($Na_2SO_4$) and then concentrated to give an oil. This was purified by column chromatography (EtOAc:hexane; 1:5) to give the sub-title compound as a mixture of separable diastereoisomers in a total of 44% yield.
(a) Diastereoisomers 1 (the less polar compound)
$^{13}C$ NMR in $CDCl_3$: δ 4.8, 4.6, 18.0, 25.7, 28.6, 33.1, 42.4, 43.3, 58.3, 58.8, 59.5, 59.9, 61.2, 61.5, 69.3, 69.8, 71.1, 71.5, 72.0, 79.1, 103.6, 115.6, 119.2, 128.4, 129.9, 133.1, 133.8, 154.9, 162.4, 165.4.
CI-MS (methane): m/z=636 ($MH^+$).
(b) Diastereoisomers 2 (the more polar compound)
CI-MS (methane): m/z=636 ($MH^+$).
$^{13}C$ NMR in $CDCl_3$: δ 4.7, 4.5, 18.0, 25.7, 28.5, 33.5, 47.6, 48.6, 53.2, 54.0, 54.5, 55.0, 62.4, 69.3, 69.7, 71.3, 71.6, 79.2, 103.6, 115.6, 119.2, 128.4, 129.5, 130.2, 133.1, 133.9, 154.7, 162.4, 165.4.

(iv) tert-Butyl 7-[3-(4-cyanophenoxy)-2-hydroxypropyl]-9-benzoyloxy-3,7-diazabicyclo[3.3.1]nonane-3-carboxylate; Diastereoisomers 1

Diastereoisomers 1 from step (iii) above (200 mg; 0.315 mmol) was mixed with tetrabutylammonium fluoride (0.47 mL; 0.47 mmol; 1.0 M in THF) in THF (2.0 mL), and stirred for 2 h at rt. The mixture was partitioned with ethyl acetate (3×20 mL) and water (20 mL), the organic layer separated, dried over $Na_2SO_4$ and then concentrated. The resulting oil was purified using column chromatography (hexane:EtOAc; 1:1) to give the sub-title compound in 79% yield.
CI-MS (methane) m/z=522 ($MH^+$)
$^{13}C$ NMR in $CDCl_3$: δ 28.6, 32.9, 33.3, 42.3, 43.5, 55.8, 59.3, 60.2, 60.7, 65.5, 70.5, 72.3, 79.9, 104.0, 115.3, 119.0, 128.4, 129.5, 129.9, 133.2, 133.8, 156.0, 162.0, 165.4.

(v) tert-Butyl 7-[3-(4-cyanophenoxy)-2-hydroxypropyl]-9-benzoyloxy-3,7-diazabicyclo[3.3.1]nonane-3-carboxylate; Diastereoisomers 2

The sub-title compound was prepared according to the procedure of step (iv) above, using Diastereoisomers 2 from step (iii) above, in 75% yield.
CI-MS (methane) m/z=522 ($MH^+$).
$^{13}C$ NMR in $CDCl_3$: δ 28.6, 33.1, 33.6, 47.3, 48.4, 49.0, 50.7, 54.4, 61.6, 65.1, 65.9, 70.7, 72.2, 80.0, 104.0, 115.3, 119.0, 128.4, 129.4, 130.0, 133.1, 133.8, 155.9, 162.1, 165.3.

Example 7 tert-Butyl 7-[3-(4-cyanophenoxy)-2-hydroxypropyl]-9-propionyloxy-3,7-diazabicyclo[3.3.1]nonane-3-carboxylate; diastereoisomers 1

(i) tert-Butyl 7-[3-(4-cyanophenoxy)-2-(tert-butyldimethylsilyloxy-propyl) 9-propionyloxy-3,7-diazabicyclo[3.3.1]nonane-3-carboxylate The sub-title compound was prepared in a 69% yield according to the procedure described in Example 6(iii) above, using propionic acid in place of benzoic acid.
CI-MS (methane): m/z =588 ($MH^+$).

(ii) tert-Butyl 7-[3-(4-cyanophenoxy)-2-hydroxypropyl]-9-propionyloxy-3,7-diazabicyclo[3.3.1]nonane-3-carboxylate; diastereoisomers 1

The title compound was prepared in 64% yield according to the procedure of Example 6(iv) above, using tert-butyl 7-[3-(4-cyanophenoxy)-2-(tert-butyldumethylsilyloxypropyl)]-9-propionyl-3,7-diazabicyclo[3.3.1]-nonane-3-carboxylate (from step (i) above).
CI-MS (methane) m/z=474 ($MH^+$).

Example 8 tert-Butyl 7-[3-(4-cyanoanilino)propyl]-9-hydroxy-3,7-diazabicyclo[3.3.1]-nonane-3-carboxylate (i) tert-Butyl 7-benzyl-9-oxy-3,7-diazabicyclo[3.3] nonane-3-carboxylate Paraformaldehyde (4.00 g; 127 mmol) was added to a solution of benzylamine (13.7 g; 126 mmol) in ethanol (190 mL). The solution was heated to 60° C. and a solution of acetic acid (15.2 g; 252 mmol) in ethanol (160 nL) was added over 2 hours. After additional stirring for 1 hour, the solution was cooled to room temperature. This solution was added (over 2 hours) to a mixture of 1-ert-butoxycarbonyl-4-piperidone (25.5 g, 127 mmol) and paraformaldehyde (4.80 g; 152 mmol) in ethanol (270 mL) which had been heated to 60° C. After reflux overnight, the solution was cooled to room temperature. The ethanol was removed by evaporation. Extractive work-up was performed in toluene:water and the material was filtered through silica in a toluene:ethyl acetate system. Evaporation of the eluant gave a solid material (37.4 g). The purity was 90 area % (HPLC) and the was yield 60%. By performing a crystallisation in IPA, a compound with a purity of 98 area % (HPLC) and a yield of 70% was obtained.

EI-MS: m/z=330 (M+).

$^{13}$C NMR (CDCl$_3$): δ 28.72, 47.71, 49.91, 50.60, 58.83, 59.16, 61.96, 80.18, 127.37; 128.45, 128.89, 137.57, 154.89, 213.66.

(ii) tert-Butyl 7-benzyl-9-hydroxy-3,7-diazabicyclo[3.3.1]nonane-3-carboxylate

Sodium borohydride (2.77 g; 73.2 mmol) was added to a cooled (0° C.), stirred solution of tert-butyl 7-benzyl-9-oxy-3,7-diazabicyclo[3.3.1]-nonane-3-carboxylate (from step (i) above; 8.01 g; 24.4 mmol) in methanol (125 mL). Once addition was complete, the reaction was stirred at rt overnight. The solvent was then evaporated and the residue re-dissolved in toluene. This solution was washed with water and brine; and the resulting organic layer then separated, dried (Na$_2$SO$_4$) and concentrated to give the sub-title compound in quantitative yield.

(iii) tert-Butyl 9-hydroxy-3,7-diazabicyclo[3.3.1]nonane-3-carboxylate

The sub-title compound was prepared in quantitative yield according to the procedure of Example 5(iv) above, using ten-butyl 7-benzyl-9-hydroxy-3,7-diazabicyclo[3.3.1]nonane-3-carboxylate in place of tert-butyl 7-benzyl-9-hydroxy-9-methyl-3,7-diazabicyclo[3.3.1]nonane-3-carboxylate.

(iv) (4-Cyanoanilino)propan-3-ol

A mixture of 4-fluorobenzonitrile (1.0 g, 8.26 mmol) and 3-aminopropanol (4.54 g, 58.7 mmol) was refluxed under an inert atmosphere (N$_2$) for 15 h. Water (500 mL) and diethyl ether (500 mL) were then added, and the resulting organic layer separated, dried (Na$_2$SO$_4$) and concentrated. The residue was purified by column chromatography (heptane:EtOAc; 1:3) to give the sub-title compound in 84% yield.

(v) (4-Cyanoanilino)propyl-3-methanesulfonate

Methanesulfonyl chloride (0.33 g, 2.9 mmol) was added to a cooled (0° C.), stirred solution of (4-cyanoanilino)propan-3-ol (from step (iv) above; 0.48 g, 2.76 mmol) and triethylamine (0.56 g, 5.54 mmol) in dichloromethane (35 mL). After addition was complete, stirring was continued at rt until all of the starting material had been consumed (as indicated by tlc). NaHCO$_3$ solution was added, and the resulting organic layer was separated, dried (Na$_2$SO$_4$) and concentrated to give the sub-title compound in quantitative yield.

(vi) tert-Butyl 7-[3-(4-cyanoanilino)propyl]-9-hydroxy-3,7-diazabicyclo-[3.3.1]nonane-3-carboxylate tert-Butyl 9-hydroxy-3,7-diazabicyclo[3.3.1]nonane-3-carboxylate (from step (iii) above; 0.84 g; 3.48 mmol) was added to a stirred suspension of anhydrous potassium carbonate (0.67 g; 4.8 mmol) and (4-cyanoanilino)propyl-3-methanesulfonate (from step (v) above; 0.89 g; 3.48 mmol) in MeCN (5 mL) under an inert atmosphere (N$_2$). The reaction mixture was stirred for 10 h at rt, before the solvent was removed under reduced pressure. The residue was partitioned between CH$_2$Cl$_2$ and NaHCO$_3$ (aq.), and then the organic layer separated, dried (Na$_2$SO$_4$) and concentrated. Purification by column chromatography gave the title compound in 41% yield.

FAB-MS: m/z=401.08 (MH$^+$)

$^{13}$C NMR in CDCl$_3$: δ 25.9, 28.5, 35.5, 41.2, 47.6, 48.6, 51.8, 52.8, 56.1, 70.0, 79.5, 97.8, 111.9, 120.6, 133.7, 151.4, 155.3

Example 9 iso-Propyl 7-[2-amino-2-(4-cyanophenyl)ethyl]-3,7-diazabicyclo[3.3.1]-nonane-3-carboxylate (i) 3,7-Dibenzyl-3,7-diazabicyclo[3.3.1]-nonane The sub-title compound was prepared according to the procedure described in *J. Org. Chem.*, 41 (1976) 1593-1597, using 3,7-dibenzyl-3,7-diazabicyclo[3.3.1]nonane-9-one (Example 5(i) above) in place of N-benzyl-N'-methylbispidone.

(ii) 3-Benzyl-3,7-diazabicyclo[3.3.1]nonane

The sub-title compound was prepared in quantitative yield according to the procedure of Example 5(iv) above, using 3,7-dibenzyl-3,7-diazabicyclo[3.3.1]nonane (from step (i) above) in place of tert-butyl 7-benzyl-9-hydroxy-9-methyl-3,7-diazabicyclo[3.3.1]nonane-3-carboxylate.

$^{13}$C NMR in CDCl$_3$: δ 30.1, 33.4, 36.0, 52.5, 59.6, 64.3, 126.9, 128.3, 128.7, 138.8.

(iii) iso-Propyl 7-benzyl-3,7-diazabicyclo[3.3.1]nonane-3-carboxylate iso-Propylchloroformate (55 mmol) and concentrated NaOH (6.0 mL; 10 M) were added, along with 10 mL of water, to a solution of 3-benzyl-3,7-diazabicyclo[3.3.1]nonane (from step (ii) above; 10.8 g; 50 mmol) in CH$_2$Cl$_2$ (50 mL). The reaction mixture was stirred for 3 h and the phases separated. The organic phase was washed with H$_2$O and brine, dried and concentrated to give the sub-title compound in 95% yield.

(iv) iso-Propyl 3,7-diazabicyclo[3.3.1]nonane-3-carboxylate

The sub-title compound was prepared in quantitative yield according to the procedure of Example 5(iv) above, using iso-propyl 7-benzyl-3,7-diazabicyclo[3.3.1]nonane-3-carboxylate (from step (iii) above) in place of tert-butyl 7-benzyl-9-hydroxy-9-methyl-3,7-diazabicyclo[3.3.1]nonane-3-carboxylate.

FAB-MS: m/z=213.2 (MH$^+$).

$^{13}$C NMR in CD$_3$CN: δ 22.53, 29.34, 32.23, 49.46, 52.40, 68.67, 156.24.

(v) iso-Propyl 7-[2-(4-cyanophenyl)-2-hydroxyethyl]-3,7-diazabicyclo-[3.3.1]nonane-3-carboxylate 4-Cyanophenacyl bromide (225 mg; 1 mmol) was added to a stirred solution of iso-propyl 3,7-diazabicyclo[3.3.1]

nonane-3-carboxylate (from step (iv) above; 212 mg; 1 mmol) in MeCN (2 mL). After stirring for 15 min at 0° C., NaBH$_4$ (40 mg; 1 mmol) was added, and the reaction was allowed to warm to rt over 45 minutes. The reaction mixture was concentrated, dissolved in CH$_2$Cl$_2$ and washed with NaHCO$_3$ (aq.) and brine. The organic layer was separated, dried and concentrated to give an oil which was purified using column chromatography (hexane:EtOAc:IPA; 50:49:1) to give the sub-title compound in 35% yield.

(vi) iso-Propyl 7-[2-(4-cyanophenyl)-2-chloroethyl]-3,7-diazabicyclo-[3.3.1 nonane-3-carboxylate Methanesulfonyl chloride (2.15 mL; 27 mmol) was added to a cooled (−10° C.), stirred solution of iso-propyl 7-[2-(4-cyanophenyl)-2-hydroxy-ethyl]-3,7-diazabicyclo[3.3.1] nonane-3-carboxylate (from step (v) above; 7.35 g; 21 mmol) in CH$_2$Cl$_2$ (30 mL). After addition, the reaction mixture was stirred at rt for 3 h. The solvent was evaporated to give the sub-title compound in a quantitative yield.

(vii) iso-Propyl 7-[2-azido-2-(4-cyanophenyl)ethyl]-3,7-diazabicyclo-[3.3.1]nonane-3-carboxylate Sodium azide (6.5 g; 100 mmol) was added to a solution of 7-[2-(4-cyanophenyl)-2-chloroethyl]-3,7-diazabicyclo [3.3.1]nonane-3-carboxylate (from step (vi) above; 7.73 g; 21 mmol) in DMF (75 mL). The resulting suspension was stirred for 12 h at rt. The reaction mixture was partitioned between CH$_2$Cl$_2$ and NaHCO$_3$ (aq.), the organic layer separated, dried and then concentrated to give the sub-title compound in 95% yield.

(viii) iso-Propyl 7-[2-amino-2-(4-cyanophenyl) ethyl]-3,7-diazabicyclo-[3.3.1]nonane-3-carboxylate A solution of iso-propyl 7-[2-azido-2-(4-cyanophenyl) ethyl]-3,7-diazabicyclo[3.3.1]nonane-3-carboxylate (from step (vii) above; 7.51 g; 19.5 mmol) in aqueous ethanol (85%) was hydrogenated over 5% Pd/C at 1 atm until tlc indicated that the reaction was complete. The catalyst was removed by filtration through a pad of Celite®, and the filtrate concentrated under reduced pressure to give the title compound in 98% yield.

FAB-MS: m/z=357.0 (MH$^+$)

$^{13}$C NMR in CDCl$_3$: δ 22.63, 30.05, 30.30, 32.50, 48.88, 49.26, 52.70, 57.53, 61.32, 68.54, 68.67, 110.97, 119.87, 128.68, 132.90, 152.56, 156.43

Example 10 iso-Propyl 7-[2-carbamoylamino-2-(4-cyanophenyl) ethyl]-3,7-diazabicyclo [3.3.1]nonane-3-carboxylate A solution of tetrahydro-2-pyranyl isocyanate (382 mg, 3.0 mmol) in benzene (10 mL) was added to a stirred solution of iso-propyl 7-[2-amino-2-(4-cyanophenyl)ethyl]-3,7-diazabicyclo[3.3.1]nonane-3-carboxylate (see Example 9 above; 1.07 g; 3.0 mmol) in benzene (35 mL). The reaction mixture was stirred for 2 h at rt, after which the solvent was evaporated and the residue re-dissolved in a mixture of MeOH (27 mL) and dilute HCl (4.5 mL; 0.1 M). The resulting solution was refluxed for 3 h, before the acid was neutralized (NaHCO$_3$) and the MeOH removed by evaporation to give a precipitate which was collected and recrystallized from IPA to give the title compound in 67% yield.

FAB-MS: m/z=399.7 (MH$^+$)

$^{13}$C NMR in CDCl$_3$: δ 22.35, 22.69, 28.67, 29.12, 32.42, 48.11, 49.15, 51.76, 55.83, 59.13, 63.54, 68.88, 110.49, 119.11, 126.62, 132.29, 149.14, 156.62, 159.76

Example 11 iso-Propyl 7-[2-carbamoylcarboxamido-2-(4-cyanophenyl)ethyl]-3,7-diazabicyclo[3.3.1]nonane-3-carboxylate iso-Propyl 7-[2-amino-2-(4-cyanophenyl)ethyl]-3,7-diazabicyclo[3.3.1]-nonane-3-carboxylate (see Example 9 above; 0.36 g; 1.0 mmol) and 1-hydroxybenzotriazole hydrate (0.28 g; 2 mmol) were added to a stirred solution of oxalic acid diamide (0.1 g; 1.1 mmol) in DMF (8 mL). Triethylamine was added until the pH reached 7-8, after which the reaction mixture was cooled to 0° C. whilst 1-(3-dimethylaminopropyl)-3-ethylcarbodiimide hydrochloride (0.23 g; 1.2 mmol) was added. The reaction mixture was then stirred at rt for 10 h, after which water (15 mL) was added and the DMF evaporated. The residue was partitioned between diethyl ether and NaHCO$_3$ (aq.), the organic layer separated, washed with water, dried and then concentrated. The resulting residue was recrystallized from MeOH and di-iso-propyl ether to give the title compound in 45% yield.

ESI-MS: m/z=428.3 (MH$^+$)

$^{13}$C NMR in CDCl$_3$: δ 22.34, 28.62, 29.58, 29.89, 48.04, 51.10, 52.03, 58.67, 59.48, 59.66, 63.65, 68.03, 111.38, 118.53, 127.25, 132.41, 145.77, 155.71, 159.24, 161.43

Example 12 iso-Propyl 7-[2-(4-cyanophenyl)-2-formamidoethyl]-3,7-diazabicyclo-[3.3.1]nonane-3-carboxylate Ethyl formate (0.5 mL) was added to a stirred solution of iso-propyl 7-[2-amino-2-(4-cyanophenyl)ethyl]-3,7-diazabicyclo[3.3.1]nonane-3-carboxylate (from Example 9(viii) above; 0.71 g; 2.0 mmol), and the reaction mixture was refluxed for 5 h. The solvent was evaporated and the residue partitioned between diethyl ether and NaOH (2 M). The organic layer was separated, washed with water, dried and then concentrated. The resulting residue was then recrystallized from MeOH and di-iso-propyl ether to give the title compound in 40% yield.

FAB-MS: m/z=384.9 (MH$^+$)

$^{13}$C NMR in CDCl$_3$: δ 22.44, 22.78, 28.68, 29.13, 32.39, 48.13, 49.17, 50.54, 56.00, 59.16, 63.07, 68.39, 110.97, 118.81, 126.68, 132.43, 147.02, 156.76, 163.01

Example 13 tert-Butyl 7-[2-amino-3-(4-cyanophenoxy)propyl]-3,7-diazabicyclo[3.3.1]-nonane-3-carboxylate (i) Benzyl 3-(4-cyanophenoxy)-2-hydroxypropylcarbamate 4-(3-Amino-2-bydroxypropoxy)benzonitrile (see Example 1(ii) above; 30.0 g; 0.156 mol) and triethylamine (23.7 g; 0.234 mol) was dissolved in 150 mL of CHCl$_3$, and cooled to 0° C. N-(Benzyloxycarbonyloxy)succinimide (42.9 g; 0.172 mol), dissolved in 150 mL of CHCl$_3$, was added dropwise. The mixture was stirred at rt overnight. The solvent was evaporated, the residue was dissolved in DCM and washed with H$_2$O (2×250 mL) and brine (250 mL), dried, and evaporated to give 51 g (100%) of the sub-title compound.

(ii) 2-{[(Benzyloxy)carbonyl]amino}-1-[(4-cyanophenoxy)methyl]ethyl methanesulfonate Benzyl 3-(4-cyanophenoxy)-2-hydroxypropylcarbamate (2 g; 6.1 mmol; from step (i) above) and a catalytic amount (10 mol %) of DMAP was mixed in 6 mL of dry pyridine. The mixture was cooled to 0° C., and methanesulfonyl chloride (0.52 mL; 1.1 eq.) was added dropwise at 0° C. The mixture was allowed to reach room temperature for 3 h. The pyridine was evaporated. Ethyl acetate was added, the solution was washed with water, and the organic layer was separated, dried and evaporated to give 2.3 g (93%) of the sub-title compound.

(iii) Benzyl 2-[(4-cyanophenoxy)methyl]-1-aziridinecarboxylate

2-{[(Benzyloxy)carbonyl]amino}-1-[(4-cyanophenoxy)methyl]ethyl methanesulfonate (47.7 mg; 0.12 mol; from step (ii) above), tetrabutylammonium hydrogensulfate (4.81 g; 0.014 mol) and 290 mL of DCM were mixed and cooled to 0° C. 97 mL of 50% NaOH was added and the mixture was stirred vigorously for 50 minutes. 500 mL of water and 500 mL of ether were added. The organic phase was separated, washed with water, dried ($Na_2SO_4$) and evaporated. Purification by chromatography on silica (DCM) gave 33.13 g (89%) of the sub-title compound.

(iv) tert-Butyl 7-benzyl-3,7-diazabicyclo[3.3.1]nonane-3-carboxylate

Di-ten-butyl dicarbonate was added slowly to a solution of 3-benzyl-3,7-diazabicyclo[3.3.1]nonane (see Example 9(ii) above; 60 g; 277 mmol) in THF (600 mL). The reaction was stirred at rt until all of the starting material had been consumed (as indicated by tlc). The solvent was then removed under reduced pressure to give a quantitative yield of the sub-title compound.

(v) tert-Butyl 3,7-diazabicyclo[3.3.1]nonane-3-carboxylate

The sub-title compound was prepared in quantitative yield according to the procedure of Example 5(iv) above, using tert-butyl 7-benzyl-3,7-diazabicyclo[3.3.1]nonane-3-carboxylate (from step (iv) above) in place of tert-butyl 7-benzyl-9-hydroxy-9-methyl-3,7-diazabicyclo[3.3.1]nonane-3-carboxylate.

$^{13}$C NMR in $CDCl_3$: δ 28.05, 28.29, 31.33, 48.35, 49.11, 51.53, 79.34, 155.16

(vi) tert-Butyl 7-[2-{[(benzyloxy)carbonyl]amino}-3-(4-cyanophenoxy)-propyl]-3,7-diazabicyclo[3.3.1]nonane-3-carboxylate Benzyl 2-[(4-cyanophenoxy)methyl]-1-aziridinecarboxylate (1.0 g; 3.2 mmol; from step (iii) above) was mixed with tert-butyl 3,7-diazabicyclo[3.3.1]nonane-3-carboxylate (from step (v) above; 0.73 g; 3.2 mmol) and 30 mL of iso-propanol, and stirred at 60° C. for 5 h, and then at rt overnight. The solvent was evaporated and the crude material was purified on silica (DCM:5% MeOH) yielding 1.3 g (76%) of sub-title compound.

(vii) tert-Butyl 7-[2-amino-3-(4-cyanophenoxy)propyl]-3,7-diazabicyclo-[3.3.1]nonane-3-carboxylate tert-Butyl 7-[2-{[(benzyloxy)carbonyl]amino}-3-(4-cyanophenoxy)propyl]-3,7-diazabicyclo[3.3.1]nonane-3-carboxylate (from step (vi) above; 3 g; 5.6 mmol) was dissolved in ethanol (95%) and hydrogenated over 5% Pd/C at 1 atm., for 2 hours. The catalyst was removed by filtration through a pad of Celite®. The residue was evaporated, and purified by chromatography (ethyl acetate: 10% MeOH). Yield: 2 g (91%).

$^{13}$C NMR in MeOD: δ 29.01, 30.43, 31.86, 59.57, 59.96, 61.63, 61.87, 62.71, 72.34, 80.93, 105.03, 116.85, 119.98, 135.25, 156.88, 163.85 (The (R)- and (S)— isomers were made from chiral 4-(2-oxiranylmethoxy)benzonitrile: 4-(2(R)-oxiranylmethoxy)benzonitrile provided the S-form of lert-butyl 7-[2-amino-3-(4-cyanophenoxy)propyl]-3,7-diazabicyclo[3.3.1] nonane-3-carboxylate, and 4-(2(S)-oxiranyl-methoxy)benzonitrile provided the R-form.)

Example 14 tert-Butyl 7-[2-amino-3-(4-cyanophenoxy)propyl]-9-hydroxy-3,7-diazabicyclo[3.3.1]nonane-3-carboxylate

(i) tert-Butyl 7-[2-{[(benzyloxy)carbonyl]amino}-3-(4-cyanophenoxy)-propyl]-9-hydroxy-3,7-diazabicyclo(3.3.1]nonane-3-carboxylate tert-Butyl 9-hydroxy-3,7-diazabicyclo[3.3.]nonane-3-carboxylate (3.85 g; 15.9 mmol; see Example 8(iii) above) was mixed with benzyl 2-[(4-cyanophenoxy)methyl]-1-aziridinecarboxylate (4.44 g, 14.4 mmol; see Example 13(iii) above) in 100 mL of iso-propanol:$H_2O$ (8:2). The mixture was stirred at 60° C. for 24 h. The solvent was evaporated and the residue was purified by chromatography on silica (toluene:ethyl acetate:iso-propanol; 8:1:1). Yield 6.21 g (78%).

(ii) tert-Butyl 7-[2-amino-3-(4-cyanophenoxy)propyl]-9-hydroxy-3,7-diazabicyclo[3.3.1]nonane-3-carboxylate tert-Butyl 7-[2-{[(benzyloxy)carbonyl]amino}-3-(4-cyanophenoxy)propyl]-9-hydroxy-3,7-diazabicyclo[3.3.1] nonane-3-carboxylate (from step (i) above; 6.17 g; 11.2 mmol) was dissolved in ethanol (56 mL; 85%) and hydrogenated over Pd/C (5%). The resultant mixture was filtered, the solvent was evaporated and the crude product was purified by chromatography on silica (toluene:ethyl acetate:isopropanol; 8:1:1) which gave 2.99 g (64%) of the tide compound.

FAB-MS: m/z=417.4 ($MH^+$)

$^{13}$C NMR in MeOD: δ 27.82, 35.77, 51.40, 51.94, 53.55, 53.91, 61.60, 68.11, 71.23, 79.81, 103.76, 115.55, 118.85, 133.98, 155.41, 162.59

Example 15 tert-Butyl 7-[3-(4-cyanoanilino)propyl]-9-hydroxy-1,5-dimethyl-3,7-diazabicyclo[3.3.1]nonane-3-carboxylate

(i) 3,7-Dibenzyl-1,5-dimethyl-9-hydroxy-3,7-diazabicyclo[3.3.1]nonane

The sub-title compound was prepared according to the procedure described in *Chem. Heterocycl. Compd.*, 30 (1994)$_{3-53}$-357.

(ii) 3-Benzyl-1,5-dimethyl-9-hydroxy-3,7-diazabicyclo[3.3.1]nonane

A solution of 3,7-dibenzyl-1,5-dimethyl-9-hydroxy-3,7-diazabicyclo-[3.3.1]nonane (from step (i) above; 2.71 g, 7.74 mmol) in aqueous ethanol (20 mL; 95%) was hydrogenated over 5% Pd/C at 1 atm. until tlc indicated that the reaction was complete. The catalyst was removed by filtration through a pad of Celite®, and the filtrate concentrated to give the sub-title compound in a quantitative yield.

(iii) tert-Butyl 7-benzyl-1,5-dimethyl-9-hydroxy-3,7-diazabicyclo[3.3.1]-nonane-3-carboxylate Di-tert-butyl dicarbonate was added slowly to a solution of 3-benzyl-1,5-dimethyl-9-hydroxy-3,7-diazabicyclo[3.3.1]nonane (from step (ii) above; 0.68 g; 2.61 mmol) in THF (5 mL). The reaction was stirred at rt until all of the starting material had been consumed (as indicated by tlc). The solvent was removed under reduced pressure to give the sub-tide compound in a 89% yield.

(iv) tert-Butyl 1,5-dimethyl-9-hydroxy-3,7-diazabicyclo[3.3.1]nonane-3-carboxylate The sub-title compound was prepared in quantitative yield according to the procedure described in step (ii) above, using tert-butyl 7-benzyl-1,5-dimethyl-9-hydroxy-3,7-diazabicyclo[3.3.1] nonane-3-carboxylate (from step (iii) above) in place of 3,7-dibenzyl-1,5-dimethyl-9-hydroxy-3,7-diazabicyclo[3.3.1]nonane.

(v) tert-Butyl 7-[3-(4-cyanoanilino)propyl]-9-hydroxy-1,5-dimethyl-3,7-diazabicyclo[3.3.1]nonane-3-carboxylate tert-Butyl 1,5-dimethyl-9-hydroxy-3,7-diazabicyclo[3.3.1]nonane-3-carboxylate (from step (iv) above; 1.05 g, 3.89 mmol) was dissolved in 10 mL of MeCN. Triethylamine (0.39 g, 3.89 mmol) and (4-cyanoanilino)propyl-3-methanesulfonate (see Example 8(v) above; 0.99 g, 3.89 mmol) were added. The reaction mixture was stirred for 72 h at 60° C., before the solvent was removed under reduced pressure. The residue was partitioned between $CH_2Cl_2$ and $NaHCO_3$ (aq.), and then the organic layer separated, dried ($Na_2SO_4$) and concentrated. Purification by column chromatography gave the tide compound in a 4% yield.

Fab-ms: m/z=429.0 (MH)+

$^1$H NMR in $CDCl_3$: δ 0.99 (s, 6h), 1.45 (s, 9h), 2.00-2.18 (m, 2h), 2.49-3.60 (m, 12h), 3.61-3.88 (m, 2h), 3.904.08 (m, 1h), 6.54-6.66 (d, 2h), 7.38-7.46 (d, 2h) example 16 the compounds of the above examples 1 to 15 were tested in test a above and were all found to exhibit $D_{10}$ values of more than 6.0.

| Abbreviations | |
|---|---|
| AcOH = | acetic acid |
| aq. = | aqueous |
| atm. = | atmospheres |
| Bu = | butyl |
| DCM = | dichloromethane |
| DMAP = | 4-dimethylaminopyridine |
| DMF = | dimethylformamide |
| EI = | electron ionisation |
| Et = | ethyl |
| EtOAc = | ethyl acetate |
| EtOH = | ethanol |
| ESI = | electron spray interface |
| FAB = | fast atom bombardment |
| h = | hours |
| IPA = | iso-propanol |
| LC = | liquid chromatography |
| HPLC = | high performance liquid chromatography |

| Abbreviations | |
|---|---|
| Me = | methyl |
| MeCN = | acetonitrile |
| MeOH = | methanol |
| min. = | minutes |
| MS = | mass spectroscopy |
| NADPH = | nicotinamide adenine dinucleotide phosphate, reduced form |
| NMR = | nuclear magnetic resonance |
| Pd/C = | palladium on carbon |
| rt. = | room temperature |
| sat. = | saturated |
| THF = | tetrahydrofuran |
| tlc = | thin layer chromatography |

Prefixes n, s, I and t have their usual meanings: normal, iso, secondary and tertiary.

What is claimed is:

1. A compound of formula 1,

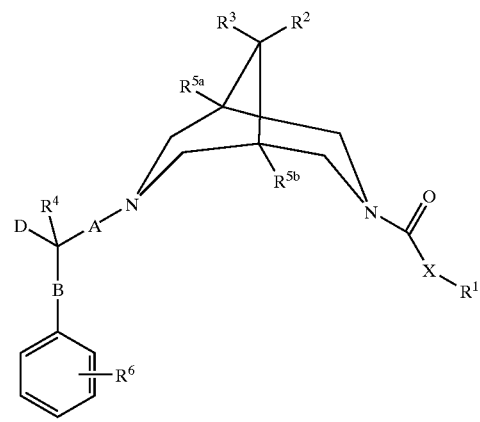

wherein $R^1$ represents $C_{12}$ alkyl, $C_{3-12}$ cycloalkyl, —$(CH_2)_a$-aryl, or $(CH_2)_a Het^1$ (all of which are optionally substituted by one or more substituents selected from —OH, halo, cyano, nitro, $C_{1-4}$alkyl, $C_{3-4}$ cycloalkyl and/or $C_{1-4}$ alkoxy or $C_{3-4}$ cycloalkoxy);

a represents 0, 1, 2, 3, or 4;

$Het^1$ represents a five to ten-membered heterocyclic ring containing one or more heteroatoms selected from oxygen, nitrogen and/or sulfur, and which also optionally includes one or more =O substituents;

X represents O or S;

$R^{5a}$ and $R^{5b}$ independently represent H, $C_{1-3}$ alkyl or $C_3$ cycloalkoxy;

$R^2$ and $R^3$ independently represent H, $C_{1-4}$ alkyl (optionally substituted with one or more nitro or cyano groups), $C_{3-4}$ cycloalkyl, $OR^7$, $N(R^{7a})R^{7b}$, $OC(O)R^8$ or together form —O—$(CH_2)_2$—O—, —$(CH_2)_3$—, —$(CH_2)_4$— or —$(CH_2)_5$—;

$R^7$ and $R^8$ independently represent H, $C_{1-6}$ alkyl, or —$(CH_2)_b$-aryl (which latter two groups are optionally substituted by one or more substituents selected from —OH, halo, cyano, nitro, $C_{1-4}$ alkyl, $C_{1-4}$ alkoxy, and/or $C_{3-4}$ cycloalkyl);

$R^{7a}$ and $R^{7b}$ independently represent H, $C_{1-6}$ alkyl or $C_{3-6}$ cycloalkyl;

b represents 0, 1, 2, 3 or 4;

$R^4$ represents H, $C_{1-6}$ alkyl or $C_{3-6}$ cycloalkyl;

D represents H, —OH, or —$(CH_2)_cN(R^{10})(R^{11})$;

c represents 0, 1, 2, 3 or 4;

$R^{10}$ represents H, $C_{1-6}$ alkyl, $C_{3-6}$ cycloalkyl, —$(CH_2)_d$-aryl, —C(NH)NH$_2$, —S(O)$_2$R$^{13}$, —[C(O)]$_e$N(R$^{14}$)(R$^{15}$), —C(O)R$^{16}$ or —C(O)OR$^{17}$;

e represents 1 or 2;

$R^{11}$ represents H, $C_{1-6}$alkyl, —C(O)R$^{18}$ or —$(CH_2)_f$-aryl (which latter group is optionally substituted by one or more substituents selected from —OH, cyano, halo, amino, nitro, $C_{1-6}$ alkyl, $C_{1-6}$alkoxy, $C_{3-6}$ cycloalkyl and/or $C_{3-6}$ cycloalkoxy);

$R^{14}$, $R^{15}$, $R^{16}$, $R^{17}$ and $R^{18}$ independently represent H, $C_{1-6}$ alkyl, $C_{3-6}$ cycloalkyl, Het$^2$ or —$(CH_2)_9$-aryl (which latter three groups are optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

$R^{13}$ represents C1.6 alkyl, $C_{3-6}$ cycloalkyl, aryl or —$(CH_2)_h$-aryl (all of which are all optionally substituted by one or more substituents chosen from halo, nitro, $C_{1-6}$ alkyl $C_{1-6}$alkoxy, C3.6 cycloalkyl and/or CO$_{36}$ cycloalkoxy);

d, f, g and h independently represent 0, 1, 2, 3 or 4;

Het$^2$ represents a five to ten-membered heterocyclic ring containing one or more heteroatoms selected from oxygen, nitrogen and/or sulfur, and which also optionally includes one or more =O substituents;

$R^6$ represents one or more optional substituents selected from —OH, cyano, halo, amino, nitro, $C_{1-6}$alkyl (optionally terminated by —N(H)C(O)OR$^{18a}$), $C_{1-6}$ alkoxy, C3.6 cycloalkyl, $C_{3-6}$ cycloalkoxy, —C(O)N(H)R$^{19}$, —NHC(O)N(H)R$^{20}$, —N(H)S(O)$_2$R$^{21}$ and/or —OS(O)$_2$R;

$R^{19}$ and $R^{20}$ independently represent H, $C_{1-6}$ alkyl or $C_{3-6}$ cycloalkyl;

$R^{18a}$, $R^{21}$ and $R^{22}$ independently represent $C_{1-6}$ alkyl or $C_{3-6}$ cycloalkyl;

A represents a single bond, $C_{1-6}$ alkylene, —N(R$^{23}$)(CH$_2$)$_j$—, —O(CH$_2$)$_j$— or —(CH$_2$)$_i$C(H)(OR$^{23}$)(CH$_2$)$_k$ (in which latter three groups, the —(CH$_2$)$_j$— group is attached to the bispidine nitrogen atom, and which latter four groups are all optionally substituted by one or more OH groups);

B represents a single bond, $C_{1-4}$ alkylene, —(CH$_2$)$_m$N(R$^{24}$)—, (CH$_2$)$_m$S(O)$_n$—, —(CH$_2$)$_m$O— (in which three latter groups, the —(CH$_2$)$_m$ group is attached to the carbon atom bearing D and R$^4$), —C(O)N(R$^{24}$)— (in which latter group, the —C(O)— group is attached to the carbon atom bearing D and R$^4$), N(R$^{24}$)C(O)O(CH$_2$)$_m$ or —N(R$^{24}$)(CH$_2$)$_m$—(in which latter two groups, the N(R$^{24}$) group is attached to the carbon atom bearing D and R$^4$);

j, k and m independently represent 0, 1, 2, 3 or 4;

n represents 0, 1 or 2;

$R^{23}$ represents H, $C_{1-6}$ alkyl, $C_{3-6}$ cycloalkyl or C(O)R$^{25}$ $R^{24}$ represents H, $C_{1-6}$ alkyl or $C_{3-6}$ cycloalkyl;

$R^{25}$ represents H, $C_{1-6}$-alkyl, $C_{3-6}$ cycloalkyl, Het$^3$ or —(C H$_2$)$_p$-aryl (which latter two groups are optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

Het$^3$ represents a five to ten-membered heterocyclic ring containing one or more heteroatoms selected from oxygen, nitrogen and/or sulfur, and which also optionally includes one or more =O substituents;

p represents 0, 1, 2, 3 or 4;

or a pharmaceutically acceptable salt, N-oxide or $C_{1-4}$ alkyl quaternary ammonium salt derivative thereof;

wherein alkyl groups that $R^1$, $R^2$, $R^3$, $R^4$, $R^{5a}$, $R^{5b}$, $R^6$, $R^7$, $R^7$, $R^{7b}$, $R^8$, $R^{10}$, R R$^{13}$, $R^{14}$, $R^{15}$, $R^{16}$, $R^{17}$ $R^{18}$, $R^{18a}$, $R^{19}$, $R^{20}$, $R^{21}$, $R^{22}$, $R^{23}$, $R^{24}$, $R^{25}$ and D may represent, and with which $R^1$, $R^7$, $R^8$, $R^{11}$, $R^{13}$, $R^{14}$, $R^{15}$, $R^{16}$, $R^{17}$, $R^{18}$ and $R^{25}$ may be substituted; and alkoxy groups that $R^6$ may represent, and with which $R^1$, $R^7$, $R^8$, $R^{11}$, $R^{13}$, $R^{14}$, $R^{15}$, $R^{16}$, $R^{17}$, $R^{18}$ and $R^{25}$ may be substituted, may be linear or, when there is a sufficient number (i.e. three) of carbon atoms, be branched and/or cycloalkyl or cycloalkyl with carbon ranges as defined above, and wherein, when there is a sufficient number (i.e. four) of carbon atoms, such alkyl and alkoxy groups may also be part cycloalkyl/acyclic or cycloalkoxy/acyclic, with carbon ranges as defined above, and wherein such alkyl and alkoxy groups may, when there is a sufficient number (i.e. two) of carbon atoms, be interrupted by oxygen and/or substituted by one or more fluoro groups; and wherein alkylene groups that A and B may represent, and —(CH$_2$)— containing groups that R, R and R$^3$ (together), $R^7$, $R^8$, $R^{10}$, $R^{11}$, $R^{13}$, $R^{14}$, $R^{15}$, $R^{16}$, $R^{17}$, $R^{18}$, $R^{25}$, A, B and D may include, may be linear or, when there is a sufficient number (i.e. two) of carbon atoms, be branched, and wherein such alkylene groups and —(CH$_2$)— containing chains may, when there is a sufficient number (i.e. two) of carbon atoms, be unsaturated and/or interrupted by oxygen;

provided that:

(a) when D represents either H or —OH, and $R^{5a}$ and $R^{5b}$ both represent H, then at least one of $R^2$ and $R^3$ represents OR$^7$, OC(O)R$^8$ or $C_{1-4}$ alkyl, which alkyl group is substituted with one or more nitro or cyano groups; and (b) when D represents —OH or —(CH$_2$)$_n$N(R$^{10}$)R$^{11}$ in which c represents 0, then:—

(i) A does not represent —N(R$^{23}$)(CH$_2$)$_j$—, —O(CH$_2$)$_j$— or —CH$_2$)$_j$C(H)(OR$^{23}$)(CH$_2$)$_k$—(in which k is 0); and/or (ii) m does not represent O when B represents —(CH$_2$)$_m$N(R$^{24}$)—, —(CH$_2$)$_m$S(O)$_n$, or —(CH$_2$)$_m$O—.

2. A compound as claimed in claim 1, wherein $R^1$ represents optionally substituted —(CH$_2$)$_a$-phenyl, in which a is 0, 1, 2 or 3.

3. A compound as claimed in claim 1, wherein $R^2$: represents H, OR$^7$, —CH$_2$NO$_2$ or —OC(O)R$^8$ or together with $R^3$—O—(CH$_2$)$_2$—O—.

4. A compound as claimed in claim 1, wherein $R^3$ represents H, OR $C_{1-4}$ alkyl or together with $R^2$ represents —O—(CH$_2$)$_2$—O—.

5. A compound as claimed in claim 1, wherein $R^4$ represents H or $C_{1-2}$ alkyl.

6. A compound as claimed in claim 1, wherein $R^{5a}$ and $R^{5b}$ either both represent H or both represent methyl.

7. A compound as claimed in claim 1, wherein $R^6$ represents one or more substituents selected from $C_{1-6}$ alkyl, cyano, nitro, amino or C(O)N(H)R$^{19}$ or N(H)S(O)$_2$R$^{21}$.

8. A compound as claimed in claim 1, wherein X represents 0.

9. A compound as claimed in claim 1, wherein A represents a single bond or linear, or branched, $C_{1-4}$ alkylene (which group is also optionally interrupted by O).

10. A compound as claimed in claim 1, wherein B represents a single bond, $C_{1-4}$ alkylene, —$(CH_2)_mO$— or —$(CH_2)_mN(R^{24})$— (in which latter two cases m is 1, 2 or 3).

11. A compound as claimed in claim 1, wherein when D represents —$(CH_2)_cN(R^{10})(R^{11})$, c represents 0, 1 or 2.

12. A compound as claimed in claim 1, wherein when D represents —$(CH_2)_nN(R^{11})(R^{11})$, $R^{10}$ represents $H_1$ $C_{1-4}$ alkyl, —$C(O)R^{16}$ (in which $R^{16}$ is H, $C_{1-3}$ alkyl or Het2), —$C(O)OR^{17}$ (in which $R^{17}$ is $C_{1-5}$ alkyl, phenyl or $C_{1-3}$ alkylphenyl), —$C(NH)NH_2$ or $[C(O)]_sN(H)R^{15}$ (in which $R_{15}$ is H or $C_{1-3}$ alkyl).

13. A compound as claimed in claim 1, wherein when D represents —$(CH)_cN(R^{10})(R^{11})$, $R^{11}$ represents H.

14. A pharmaceutical formulation including a compound as defined in claim 1 in admixture with a pharmaceutically-acceptable adjuvant, diluent or carrier.

15. A method of prophylaxis or treatment of an arrhythmia which method comprises administration of a therapeutically effective amount of a compound as defined in claim 1 to a person in need thereof.

16. A process for the preparation of a compound of formula I as defined in claim 1 which comprises:

(a) reaction of a compound of formula II,

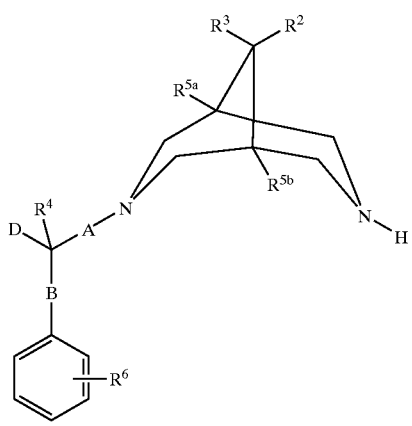

(II)

wherein $R^2$, $R^3$, $R^4$, $R^{5a}$, $R^{5b}$, $R^6$, A, B and D are as defined in claim 1 with a compound of formula III,

$R^1XC(O)L^1$     (III)

wherein $L^1$ represents a leaving group and R' and X are as defined in claim 1;

(b) for compounds of formula I in which A represents $CH_2$ and D represents —OH or $N(R^{10})H$, reaction of a compound of formula IV,

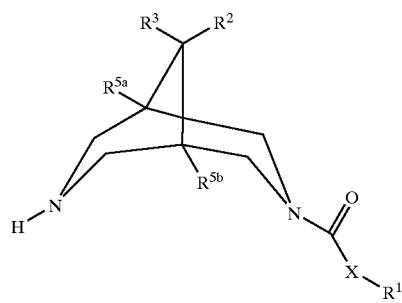

IV wherein R', $R^2$, $R^3$, $R^{5a}$, $R^{5b}$ and X are as defined in claim 1, with a compound of formula V,

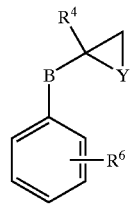

V wherein Y represents O or $N(R^{10})$ and $R^4$, $R^6$, $R^{10}$ and B are as defined in claim 1;

(c) reaction of a compound of formula IV, as defined above, with a compound of formula VI,

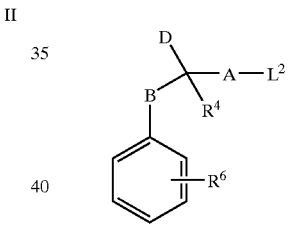

VI wherein $L^2$ represents a leaving group and $R^4$, $R^6$, A, B and D are as defined in claim 1;

(d) for compounds of formula I in which D represents H or OH and $R^4$ represents H, reduction of a compound of formula VII,

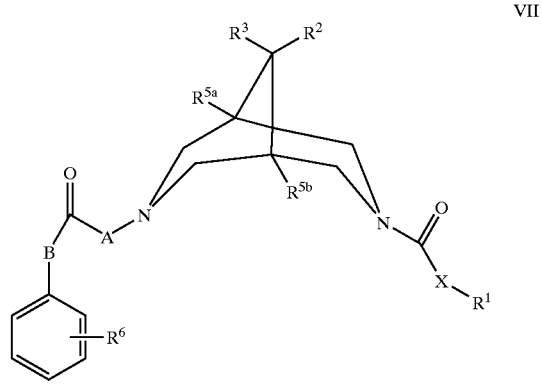

VII wherein R', $R^2$, $R^3$, $R^{5a}$, $R^{5b,\ R^6}$, A, B and X are as defined in claim 1;

(e) for compounds of formula I in which one of $R^2$ and $R^3$ represents H or OH and the other represents H, reduction of a corresponding compound of formula VIII,

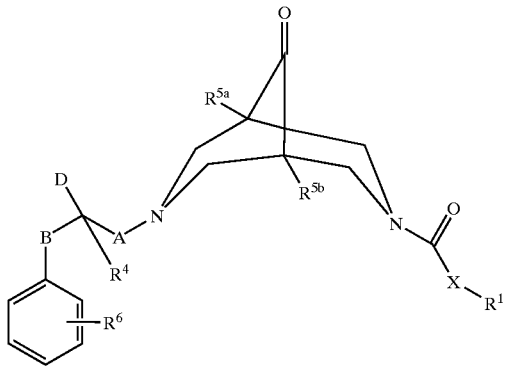

VIII wherein $R^1$, $R^4$, $R^{5a}$, $R^{5b}$, $R^6$, A, B, D and X are as defined in claim 1;

(f) for compounds of formula I in which $R^2$ and/or $R^3$ represents $OC(O)R^8$ and $R^6$ is as defined in claim 1, coupling of a corresponding compound of formula I in which $R^2$ and/or $R^3$ (as appropriate) represents OH and a compound of formula VIIIA, $$R^8CO_2H \qquad \text{VIIIA}$$

wherein $R^8$ is as defined in claim 1;

(g) for compounds of formula I in which D represents $-(CH_2)_cNH_2$ reduction of a corresponding compound of formula IX,

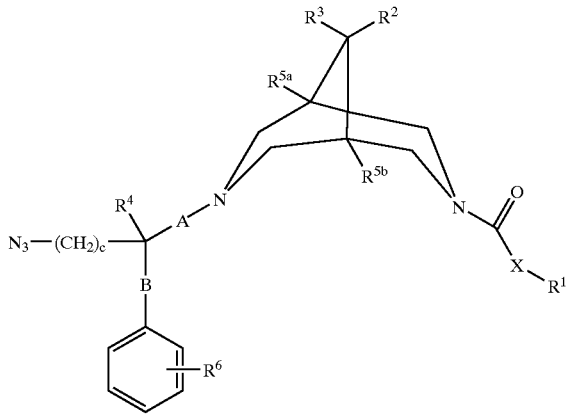

IX wherein c, $R^1$, $^2$, $R^3$, $R^4$, $R^{5a}$, $R^{5b}$, $^6$, A, B and X are as defined in claim 1;

(h) for compounds of formula I in which D represents $-N(R^{11})C(O)NH(15)$, in which $R^{11}$ and $R^{15}$ are as defined in claim 1 except that $R^{11}$ does not represent $C(O)R^{18}$, reaction of a corresponding compound of formula I in which D represents $-N(R^{11})H$, in which $R^{11}$ is as defined in claim 1 except that is does not represent $C(O)R^{18}$ in which $R^{18}$ is as defined in claim 1, with a compound of formula X, $$R^{15}N=C=O \qquad X$$

wherein $R^{15}$ is as defined in claim 1;

(i) for compounds of formula I in which D represents $-N(H)[C(O)]_2NH_2$, reaction of a corresponding compound of formula I in which D represents $-NH_2$ with oxalic acid diamide;

(j) for compounds of formula I in which D represents $-N(R^{11})C(O)R^6$, in which $R^{11}$ and $R^{16}$ are as defined in claim 1 except that $R^{11}$ does not represent $C(O)R^{18}$, reaction of a corresponding compound of formula I in which D represents $-N(R^{11})H$, in which $R^{11}$ is as defined in claim 1 except that is does not represent $C(O)R^{18}$ in which $R^{18}$ is as defined in claim 1, with a compound of formula XI $$R^{16}C(O)R_x \qquad XI$$

wherein $R_x$ represents a suitable leaving group and $R^{16}$ is as defined in claim 1;

(k) for compounds of formula I in which D represents $-N(H)R^{10}$ and $R^{10}$ is as defined in claim 1 except that it does not represent H or $-C(NH)NH_2$, reaction of a corresponding compound of formula I wherein D represents $-NH_2$ with a compound of formula XIA, $$R^{10a}L^1 \qquad XIA$$

wherein $R^{10a}$ represents $R^{10}$ as defined in claim 1 except that it does not represent H or $-C(NH)NH_2$ and $L^1$ is as defined above;

(l) for compounds of formula I which are bispidine-nitrogen N-oxide derivatives, oxidation of the corresponding bispidine nitrogen of a corresponding compound of formula I;

(m) for compounds of formula I which are $C_{1-4}$ alkyl quaternary ammonium salt derivatives, in which the alkyl group is attached to a bispidine nitrogen, reaction, at the bispidine nitrogen, of a corresponding compound of formula I with a compound of formula XII $$R^aHal \qquad XII$$

wherein $R^a$ represents $C_{1-4}$ alkyl and Hal represents Cl, Br or I;

(n) for compounds of formula I in which D and $R^4$ both represent H, A represents $C_{1-6}$alkylene, B represents $N(R^{24})(CH_2)_m$, and m and $R^{24}$ are as defined in claim 1, reaction of a compound of formula XIII,

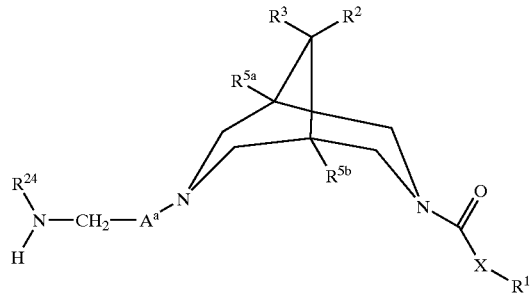

XIII wherein $A^a$ represents $C_1-$ alkylene and $R^1$, $R^2$, $R^3$, $R^5$, $R^{5b}$, $R^{24}$ and X are as defined in claim 1 with a compound of formula XIV,

XIV

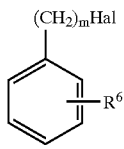

wherein R[6], m are as defined in claim 1 and Hal is as defined above;

(o) reaction of a compound of formula II, as defined above, with a compound of formula XV,

R[1]XH  XV wherein R[1] and X are as defined in claim 1, in the presence of 1,1'-carbonyldiimidazole;

(p) for compounds of formula I in which one of R[2] and R[3] represents —NH$_2$ and the other represents H, reduction of a compound of formula XVA,

XVA

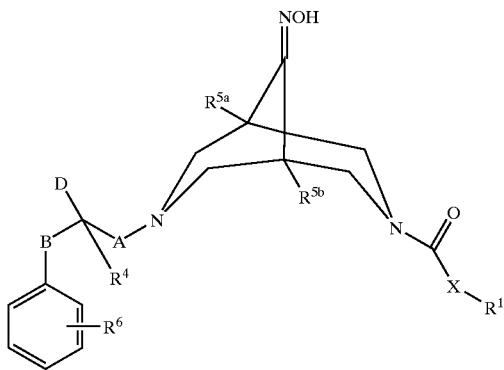

wherein R[1], R[4], R[5a], R[5b], R[6], A, B, D and X are as defined in claim 1; or (q) for compounds of formula I in which one or both of R[2] and R[3] represent —N(R[7a])R[7b] in which one or both or R[7a] and R[7b] represents $C_{1-6}$ alkyl, alkylation of a corresponding compound of formula I in which R[2] and/or R[3] represent —N(R[7a])R[7b] (as appropriate) in which R[7a] and/or R[7b] (as appropriate) represent H, using a compound of formula XXIB, R[7c]L[1]  XXIB wherein R[7c] represents $C_{1-6}$ alkyl and L[1] is as defined above.

17. A compound of formula II

II

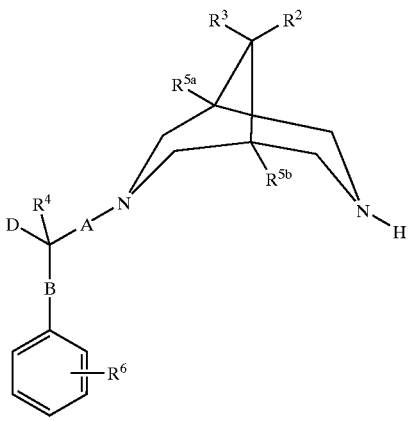

wherein R[5a] and R[5b] independently represent H, $C_{1-3}$ alkyl or $C_3$ cycloalkoxy;

R[2] and R[3] independently represent H, $C_{1-4}$ alkyl (optionally substituted with one or more nitro or cyano groups), $C_{3-4}$ cycloalkyl, OR[7], N(R[7a]) R[7b], OC(O)R[8] or together form —O—(CH$_2$)$_2$—O—, —(CH$_2$)$_3$—, —(C H$_2$)$_4$— or —(CH$_2$)$_5$—;

R[7] and R[8] independently represent H, $C_{1-6}$ alkyl, or —(CH$_2$)$_b$-aryl (which latter two groups are optionally substituted by one or more substituents selected from —OH, halo, cyano, nitro, $C_{1-4}$ alkyl, $C_{1-4}$ alkoxy, and/or $C_{3-4}$ cycloalkyl);

R[7a] and R[7b] independently represent H, $C_{1-6}$ alkyl or $C_{3-6}$ cycloalkyl;

b represents 0, 1, 2, 3 or 4;

R[4] represents H, $C_{1-6}$ alkyl or $C_{3-6}$ cycloalkyl;

D represents H, —OH, or —(CH$_2$)$_n$N(R[10])(R[11]);

c represents 0, 1, 2, 3 or 4;

R[10] represents H, $C_{1-6}$ alkyl, $C_{3-6}$ cycloalkyl, —(CH$_2$)$_d$-aryl, —C(NH)NH$_2$, —S(O)$_2$R[13], —[C(O)]$_e$N(R[4])(R[15]), —C(O)R[16] or —C(O)OR[17];

e represents 1 or 2;

R[11] represents H, $C_{1-6}$alkyl, —C(O)R[18] or —(CH$_2$)$_f$-aryl (which latter group is optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

R[14], R[15], R[16], R[17] and R[18] independently represent H, $C_{1-6}$alkyl, $C_{3-6}$ cycloalkyl, Het[2] or —(CH$_2$)$_g$-aryl (which latter three groups are optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

R[13] represents $C_{1-6}$ alkyl, $C_{3-6}$ cycloalkyl, aryl or —(CH$_2$)$_h$- aryl (all of which are all optionally substituted by one or more substituents chosen from halo, nitro, $C^{1-6}$ alkyl $C_{1-6}$ alkoxy, $C_{3-6}$ cycloalkyl and/or $C_{3-6}$ cycloalkoxy);

d, f, g and h independently represent 0, 1, 2, 3 or 4;

Het[2] represents a five to ten-membered heterocyclic ring containing one or more heteroatoms selected from oxygen, nitrogen and/or sulfur, and which also optionally includes one or more =O substituents;

43

R$^6$ represents one or more optional substituents selected from —OH, cyano, halo, amino, nitro, C$_{1-6}$ alkyl (optionally terminated by —N(H)C(O)OR$^{18a}$), C$_{1-6}$ alkoxy, C$_{3-6}$ cycloalkyl, C$_{3-6}$ cycloalkoxy, —C(O)N(H)R$^{19}$, —NHC(O)N(H)R$^{20}$, —N(H)S(O)$_2$R$^{21}$ and/or —OS(O)$_2$R$^{22}$;

R$^{19}$ and R$^{20}$ independently represent H, C$_{1-6}$ alkyl or C$_{3-6}$ cycloalkyl;

R$^{18a}$, R$^{21}$ and R$^{22}$ independently represent C$_{1-6}$ alkyl or C$_{3-6}$ cycloalkyl;

A represents a single bond, C$_{1-6}$ alkylene, —N(R$^{23}$)(CH$_2$)$_j$—, —O(CH$_2$)$_j$— or —(CH$_2$)C(H)(OR$^{23}$)(CH$_2$)$_j$— (in which latter three groups, the —(CH$_2$)$_j$— group is attached to the bispidine nitrogen atom, and which latter four groups are all optionally substituted by one or more OH groups);

B represents a single bond, C$_{1-4}$ alkylene, —(CH$_2$)$_m$N(R$^{24}$)—, (CH$_2$)$_m$S(O)$_n$—, —(CH$_2$)]O— (in which three latter groups, the —(CH$_2$)$_m$— group is attached to the carbon atom bearing D and R$^4$), —C(O)N(R$^{24}$)— (in which latter group, the —C(O)— group is attached to the carbon atom bearing D and R$^4$), N(R$^{24}$)C(O)O(CH$_2$)$_m$— or —N(R$^{24}$)(CH$_2$)$_m$(in which lattertwo groups, the N(R$^{24}$) group is attached to the carbon atom bearing D and R$^4$);

j, k and m independently represent 0, 1, 2, 3 or 4;

n represents 0, 1 or 2;

R$^{23}$ represents H, C$_{1-6}$ alkyl, C$_{3-6}$ cycloalkyl or C(O)R$^{25}$

R$^{24}$ represents H, C$_{1-6}$ alkyl or C$_{3-6}$ cycloalkyl;

R$^{25}$ represents H, C$_{1-6}$ alkyl, C$_{3-6}$ cycloalkyl, Het$^3$ or —(CH$_2$)$_p$-aryl (which latter two groups are optionally substituted by one or more substituents selected from —OH, cyano, halo, amino, nitro, C$_{1-6}$ alkyl, C$_{1-6}$ alkoxy, C$_{3-6}$ cycloalkyl and/or C$_{3-6}$ cycloalkoxy);

Het$^3$ represents a five to ten-membered heterocyclic ring containing one or more heteroatoms selected from oxygen, nitrogen and/or sulfur, and which also optionally includes one or more =O substituents;

p represents 0, 1, 2, 3 or 4;

wherein alkyl groups that R$^2$, R$^3$, R$^4$, R$^5$, R$^b$, R$^6$, R$^7$, R$^{7a}$, R$^{7b}$, R$^8$, R, R, R$^{13}$ R$^{14}$ R$^{15}$, R$^{16}$, R$^7$ R$^{18}$, R$^1$, R$^{19}$, R$^{20}$, R$^{21}$ R$^{22}$, R$^{23}$, R$^{24}$, R$^{25}$ and D may represent, and with which R$^7$, R$^8$, R$^{11}$, R$^{13}$ R$^{14}$, R$^{15}$, R$^{16}$, R$^{17}$ R$^{16}$ and R$^{25}$ may be substituted; and alkoxy groups that R$^6$ may represent, and with which R$^7$, R$^8$, R$^{11}$, R$^{13}$, R$^{14}$, R$^{15}$, R$^{16}$, R$^{17}$, R$^{18}$ and R$^{25}$ may be substituted, may be linear or, when there is a sufficient number (i.e. three) of carbon atoms, be branched and/or cycloalkyl or cycloalkoxy with carbon ranges as defined above, and wherein, when there is a sufficient number (i.e. four) of carbon atoms, such alkyl and alkoxy groups may also be part cycloalkyl/acyclic or cycloalkoxy/acyclic with carbon ranges as defined above, and wherein such alkyl and alkoxy groups may, when there is a sufficient number (i.e. two) of carbon atoms, be interrupted by oxygen and/or substituted by one or more fluoro groups; and wherein alkylene groups that A and B may represent, and —(CH$_2$)— containing groups that R$^2$ and R$^3$

44

(together), R$^7$, R$^8$, R$^{10}$, R$^{11}$, R$^3$, R$^{14}$, R R$^{16}$, R$^{17}$, R$^{18}$, R$^{25}$, A, B and D may include, may be linear or, when there is a sufficient number (i.e. two) of carbon atoms, be branched, and wherein such alkylene groups and —(CH$_2$)— containing chains may, when there is a sufficient number (i.e. two) of carbon atoms, be interrupted by oxygen, provided that when R$^{5a}$ and R$^{5b}$ both represent H, then D does not represent H or OH.

18. A compound of formula IV

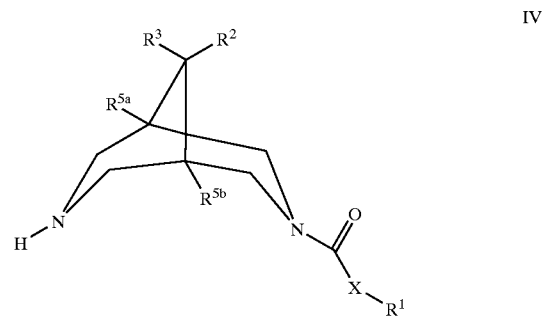

IV wherein R$^1$ represents C$_{1-12}$ alkyl, C$_{3-12}$ cycloalkyl, —(CH$_2$)$_a$-aryl, or (CH$_2$)$_a$Het$^1$ (all of which are optionally substituted by one or more substituents selected from —OH, halo, cyano, nitro, C$_{1-4}$alkyl, C$_{3-4}$ cycloalkyl and/or C$_{1-4}$ alkoxy or C$_{3-4}$ cycloalkoxy);

a represents 0, 1, 2, 3, or 4;

Het$^1$ represents a five to ten-membered heterocyclic ring containing one or more heteroatoms selected from oxygen, nitrogen and/or sulfur, and which also optionally includes one or more =O substituents;

X represents O or S;

R$^{5a}$ and R$^{5b}$ independently represent H, C$_{1-3}$ alkyl or C$_3$ cycloalkoxy;

R$^2$ and R$^3$ independently represent H, C$_{1-4}$ alkyl (optionally substituted with one or more nitro or cyano groups), C$_{3-4}$ cycloalkyl, OR$^7$, N(R$^{7a}$)R$^{7b}$, OC(O)R$^8$ or together form —O—(CH$_2$)$_2$—O—, —(CH$_2$)$_3$—, —(CH$_2$)$_4$— or —(CH$_2$)$_5$—;

R$^7$ and R$^8$ independently represent H, C$_{1-6}$ alkyl, or —(CH$_2$)$_b$-aryl or (which latter two groups are optionally substituted by one or more substituents selected from —OH, halo, cyano, nitro, C$_{1-4}$ alkyl, C$_{1-4}$ alkoxy, and/or C$_{3-4}$ cycloalkyl);

R$^{7a}$ and R$^{7b}$ independently represent H, C$_{1-6}$ alkyl or C$_{3-6}$ cycloalkyl;

b represents 0, 1, 2, 3 or 4;

wherein alkyl groups that R$^1$, R$^2$, R$^3$, R$^{5a}$, R$^{5b}$, R$^7$, R$^{7a}$, R$^{7b}$ and R$^8$ may represent, and with which R$^1$, R$^7$ and R$^8$ may be substituted; and alkoxy groups and with which R$^1$, R$^7$ and R$^8$ may be substituted, may be linear or, when there is a sufficient number (i.e. three) of carbon atoms, be branched and/or cycloalkyl or cycloalkoxy with carbon ranges as defined above, and wherein, when there is a sufficient number (i.e. four) of carbon atoms, such alkyl and alkoxy groups may also be part cycloalkyl/acyclic or cycloalkoxy/acyclic with carbon ranges as defined above, and wherein such alkyl and alkoxy groups may, when there is a sufficient number (i.e. two) of carbon atoms, be interrupted by oxygen and/or substituted by one or more fluoro groups;

provided that when $R^{5a}$ and $R^{5b}$ both represent H, then at least one of $R^2$ and $R^3$ represents $OR^7$, $OC(O)R^8$ or $C_{1-4}$ alkyl, which alkyl group is substituted with one or more nitro or cyano groups.

19. A compound of formula VIII

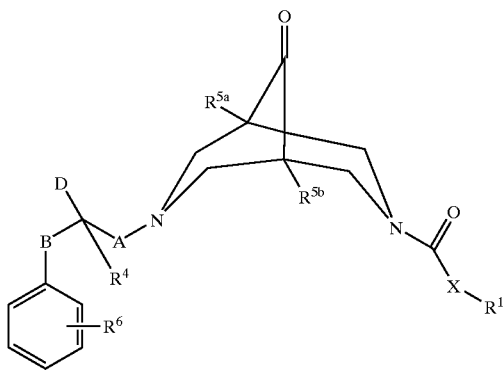

VIII wherein $R^1$ represents $C_{1-12}$alkyl, $C_{3-12}$ cycloalkyl, —$(CH_2)_a$-aryl, or $(CH_2)_a$Het$^1$ (all of which are optionally substituted by one or more substituents selected from —OH, halo, cyano, nitro, $C_{1-4}$alkyl, $C_{3-4}$ cycloalkyl and/or $C_{1-4}$ alkoxy or $C_{3-4}$ cycloalkoxy);

a represents 0, 1, 2, 3, or 4;

Het$^1$ represents a five to ten-membered heterocyclic ring containing one or more heteroatoms selected from oxygen, nitrogen and/or sulfur, and which also optionally includes one or more =O substituents;

X represents O or S;

$R^{5a}$ and $R^{5b}$ independently represent H, $C_{3-6}$ alkyl or $C_3$ cycloalkoxy;

$R^4$ represents H, $C_{1-6}$ alkyl or $C_{3-6}$ cycloalkyl;

D represents H, —OH, or —$(CH_2)_n N(R^{10})(R^1)$;

c represents 0, 1, 2, 3 or 4;

$R^{10}$ represents H, $C_{1-6}$ alkyl, $C_{3-6}$ cycloalkyl, —$(CH_2)_d$-aryl, —C(NH)NH$_2$, —S(O)$_2$R$^{13}$, —[C(O)]$_e$N(R$^{14}$)(R$^{15}$), —C(O)R$^{16}$ or —C(O)OR$^{17}$;

e represents 1 or 2;

$R^{11}$ represents H, $C_{1-6}$ alkyl, —C(O)R$^{18}$ or —$(CH_2)_f$-aryl (which latter group is optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

$R^{14}$, R's, $R^{16}$, $R^{17}$ and $R^{18}$ independently represent H, $C_{1-6}$alkyl, $C_{3-6}$ cycloalkyl, Het$^2$ or —$(CH_2)_g$-aryl (which latter three groups are optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

$R^{13}$ represents $C_{1-6}$ alkyl, $C_{3-6}$ cycloalkyl, aryl or —$(CH_2)_h$-aryl (all of which are all optionally substituted by one or more substituents chosen from halo, nitro, $C_{1-6}$ alkyl $C_{1-6}$ alkoxy, $C_{3-6}$ cycloalkyl and/or $C_{3-6}$ cycloalkoxy);

d, f, g and h independently represent 0, 1, 2, 3 or 4;

Het$^2$ represents a five to ten-membered heterocyclic ring containing one or more heteroatoms selected from oxygen, nitrogen and/or sulfur, and which also optionally includes one or more =O substituents;

$R^6$ represents one or more optional substituents selected from —OH, cyano, halo, amino, nitro, $C_{1-6}$alkyl (optionally terminated by —N(H)C(O)OR$^{18a}$), $C_{1-6}$ alkoxy, $C_{3-6}$ cycloalkyl, $C_{3-6}$ cycloalkoxy, —C(O)N(H)R$^{19}$, —NHC(O)N(H)R$^{20}$, —N(H)S(O)$_2$R$^{21}$ and/or —OS(O)$_2$R$^{22}$;

$R^{19}$ and $R^{20}$ independently represent H, $C_{1-6}$ alkyl or $C_{3-6}$ cycloalkyl;

$R^{18a}$, $R^{21}$ and $R^{22}$ independently represent $C_{1-6}$ alkyl or $C_{3-6}$ cycloalkyl;

A represents a single bond, $C_{1-6}$ alkylene, —N(R$^{23}$)(CH$_2$)$_j$—O(CH$_2$)$_1$— or —(CH$_2$)$_j$(H)(OR$^{23}$)(CH$_2$)$_k$— (in which latter three groups, the —(CH$_2$)$_j$— group is attached to the bispidine nitrogen atom, and which latter four groups are all optionally substituted by one or more OH groups);

B represents a single bond, $C_{1-4}$ alkylene, —(CH$_2$)$_m$N(R$^{24}$)—(CH$_2$)$_m$S(O)$_n$—, —(CH$_2$)$_m$O— (in which three latter groups, the —(CH$_2$)$_m$— group is attached to the carbon atom bearing D and $R^4$), —C(O)N(R$^{24}$)— (in which latter group, the —C(O)— group is attached to the carbon atom bearing D and $R^4$), N(R$^{24}$)C(O)O(CH$_2$)$_m$— or —N(R$^{24}$)(CH$_2$)$_m$-(in which latter two groups, the N(R$^{24}$) group is attached to the carbon atom bearing D and $R^4$);

j, k and m independently represent 0, 1, 2, 3 or 4;

n represents 0, 1 or 2;

$R^{23}$ represents H, $C_{1-6}$ alkyl, $C_{3-6}$ cycloalkyl or C(O)R$^{25}$ $R^{24}$ represents H, $C_{1-6}$ alkyl or $C_{3-6}$ cycloalkyl;

$R^{25}$ represents H, $C_{1-6}$ alkyl, $C_{3-6}$ cycloalkyl, Het$^3$ or —(CH$_2$)$_p$-aryl (which latter two groups are optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

Het$^3$ represents a five to ten-membered heterocyclic ring containing one or more heteroatoms selected from oxygen, nitrogen and/or sulfur, and which also optionally includes one or more =O substituents;

p represents 0, 1, 2, 3 or 4;

wherein alkyl groups that $R^1$, $R^4$, $R^{5a}$, $R^{5b}$, $R^6$, R, $R^a$, $R^b$, $R^8$, $R^{10}$, $R^{11}$, $R^{13}$ $R^{14}$ $R^{15}$, $R^{16}$, $R^{17}$, $R^{18}$, $R^{18a}$, $R^{19}$, $R^{20}$, $R^{21}$, $R^{22}$, $R^{23}$, $R^{24}$, $R^{25}$ and D may represent, and with which $R^1$, $R^7$, $R^8$, $R^{11}$ $R^{13}$, $R^{14}$, $R^{15}$ $R^{16}$ $R^{17}$ $R^{18}$ and $R^{25}$ may be substituted; and alkoxy groups that $R^5$ may represent, and with which $R^1$, $R^7$, $R^8$, $R^{11}$, $R^{13}$, $R^{14}$, $R^5$, $R^{16}$, $R^{17}$, $R^{18}$ and $R^{25}$ may be substituted, may be linear or, when there is a sufficient number (i.e. three) of carbon atoms, be branched and/or cycloalkyl or cycloalkoxy with carbon ranges as defined above, and wherein, when there is a sufficient number (i.e. four) of carbon atoms, such alkyl and alkoxy groups may also be part cycloalkyVacyclic or cycloalkoxy/acyclic with carbon ranges as defined above, and wherein such alkyl and alkoxy groups may, when there is a sufficient number (i.e. two) of carbon atoms, be interrupted by oxygen and/or substituted by one or more fluoro groups; and wherein alkylene groups that A and B may represent, and —(CH$_2$)— containing groups that $R^1$, $R^7$, $R^8$, $R^{10}$, $R^{11}$, $R^{13}$, $R^{14}$, $R^{15}$, $R^{16}$, $R^{17}$, $R^{18}$, $R^{25}$, A, B and D may include, may be linear or, when there is a sufficient number (i.e. two) of carbon atoms, be branched, and wherein such alkylene groups and —(CH$_2$)— containing chains may, when there is a sufficient number (i.e. two) of carbon atoms, be interrupted by oxygen, provided that when $R^{5a}$ and $R^{5b}$ both represent H, then D does not represent H or OH.

20. A compound of formula XVII,

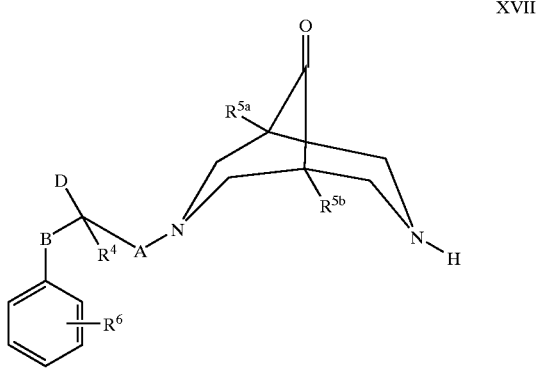

XVII wherein $R^4$, $R^{5a}$, $R^{5b}$, $R^6$, A, B and D are as defined in claim 1, provided that when $R^{5a}$ and $R^{5b}$ both represent H, then D does not represent H or OH.

21. A process for the preparation of a compound of formula VIII,

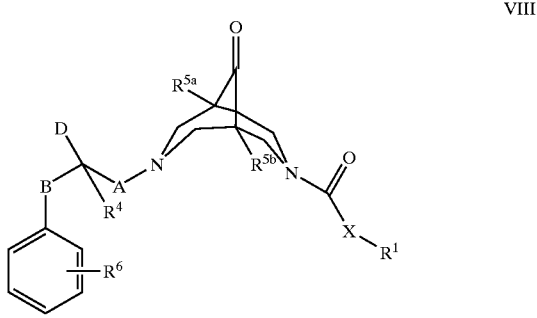

VIII wherein $R^1$ represents $C_{1-2}$ alkyl, $C_{3-12}$ cycloalkyl, —(CH$_2$)$_a$-aryl, or (CH$_2$)$_a$Het$^1$ (all of which are optionally substituted by one or more substituents selected from —OH, halo, cyano, nitro, $C_{1-4}$ alkyl, $C_{3-4}$ cycloalkyl and/or $C_{1-4}$ alkoxy or $C_{3-4}$ cycloalkoxy);

a represents 0, 1, 2, 3, or 4;

Het$^1$ represents a five to ten-membered heterocyclic ring containing one or more heteroatoms selected from oxygen, nitrogen and/or sulfur, and which also optionally includes one or more =O substituents;

X represents O or S;

$R^{5a}$ and $R^{5b}$ independently represent H, $C_{1-3}$ alkyl or C3 cycloalkoxy;

$R^4$ represents H, $C_{1-6}$ alkyl or $C_{3-6}$ cycloalkyl;

D represents H, —OH, or —(CH$_2$):N($R^{10}$)($R^1$);

c represents 0, 1, 2, 3 or 4;

$R^{10}$ represents H, $C_{1-6}$alkyl, $C_{3-6}$cycloalkyl, —(CH$_2$)$_d$-aryl, —C(NH)NH$_2$, —S(O)$_2$R$^{13}$, —[C(O)]$_e$N(R$^{14}$)(R$^{15}$), —C(O)R$^{16}$ or —C(O)OR$^{17}$;

e represents 1 or 2;

$R^{11}$ represents H, $C_{1-6}$alkyl, —C(O)R$^{18}$ or —(CH$_2$)$_f$-aryl (which latter group is optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

$R^{14}$, $R^{15}$, $R^{16}$, $R^{17}$ and $R^{18}$ independently represent H, $C_{1-6}$ alkyl, $C_{3-6}$ cycloalkyl, Het2 or —(CH$_2$)$_g$-aryl (which latter three groups are optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

$R^{13}$ represents $C_{1-6}$ alkyl, $C_{3-6}$ cycloalkyl, aryl or —(CH$_2$)$_h$-aryl (all of which are all optionally substituted by one or more substituents chosen from halo, nitro, $C_1$ alkyl $C_{1-6}$ alkoxy, $C_{3-6}$ cycloalkyl and/or $C_{1-6}$ cycloalkoxy);

d, f, g and h independently represent 0, 1, 2, 3 or 4;

Het$^2$ represents a five to ten-membered heterocyclic ring containing one or more heteroatoms selected from oxygen, nitrogen and/or sulfur, and which also optionally includes one or more =O substituents;

$R^6$ represents one or more optional substituents selected from —OH, cyano, halo, amino, nitro, $C_{1-6}$ alkyl (optionally terminated by —N(H)C(O)OR$^{18a}$), $C_{1-6}$ alkoxy, $C_{3-6}$ cycloalkyl, $C_{3-6}$ cycloalkoxy, —C(O)N(H)R$^{19}$, —NHC(O)N(H)R$^{20}$, —N(H)S(O)$_2$R$^{21}$ and/or —OS(O)$_2$R$^{22}$;

$R^{19}$ and $R^{20}$ independently represent H, $C_{1-6}$ alkyl or $C_{3-6}$ cycloalkyl;

$R^{18a}$, $R^{21}$ and $R^{22}$ independently represent $C_{1-6}$ alkyl or $C_{3-6}$ cycloalkyl;

A represents a single bond, $C_{1-6}$ alkylene, —N(R$^{23}$)(CH$_2$)$_j$—, —O(CH$_2$)$_j$— or —(CH$_2$)$_i$C(H)(OR$^{23}$)(CH$_2$)$_k$—(in which latter three groups, the —(CH$_2$)$_j$— group is attached to the bispidine nitrogen atom, and which latter four groups are all optionally substituted by one or more OH groups);

B represents a single bond, $C_{1-4}$ alkylene, —(CH$_2$)$_m$N(R$^{24}$)—, (CH$_2$)$_m$S(O)$_n$—, —(CH$_2$)$_m$O— (in which three latter groups, the —(CH$_2$)$_m$— group is attached to the carbon atom bearing D and R$^4$), —C(O)N(R$^{24}$)— (in which latter group, the —C(O)— group is attached to the carbon atom bearing D and R$^4$), N(R$^{24}$)C(O)O(CH$_2$)$_m$— or —N(R$^{24}$)(CH$_2$)$_m$—(in which latter two groups, the N(R$^{24}$) group is attached to the carbon atom bearing D and R$^4$);

j, k and m independently represent 0, 1, 2, 3 or 4;

n represents 0, 1 or 2;

$R^{23}$ represents H, $C_{1-6}$ alkyl, $C_{3-6}$ cycloalkyl or C(O)R$^{25}$ $R^{24}$ represents H, $C_{1-6}$ alkyl or $C_{3-6}$ cycloalkyl;

$R^{25}$ represents H, $C_{1-6}$ alkyl, $C_{3-6}$ cycloalkyl, $Het^3$ or —$(CH_2)_p$-aryl (which latter two groups are optionally substituted by one or more substituents selected from —OH, cyano, halo, amino, nitro, $C_{1-6}$ alkyl, $C_{1-6}$ alkoxy, $C_{3-6}$ cycloalkyl and/or $C_{3-6}$ cycloalkoxy);

$Het^3$ represents a five to ten-membered heterocyclic ring containing one or more heteroatoms selected from oxygen, nitrogen and/or sulfur, and which also optionally includes one or more =O substituents;

p represents 0, 1, 2, 3 or 4;

wherein alkyl groups that $R^1$, $R^4$, $R^{5a}$, $R^{5b}$, $R^6$, $R^7$, $R^{7a}$, $R^{7b}$, R, $R^o$, $R^{11}$, $R^{13}$, $R^{14}$ $R^{15}$, $R^{16}$ $R^{17}$ $R^{18}$, $R^{18a}$, $R^{19}$, $R^{20}$, $R^{21}$, $R^{22}$, $R^{23}$, $R^{24}$, $R^{25}$ and D may represent, and with which $R^1$, $R^7$, $R^8$, $R^{11}$, $R^{13}$, $R^{14}$, $R^{15}$, $R^{16}$, $R^{17}$, $R^{18}$ and $R^{25}$ may be substituted; and alkoxy groups that $R^6$ may represent, and with which $R^1$, $R^7$, $R^8$, $R^{11}$, $R^{13}$, $R^{14}$, $R^{15}$, $R^{16}$, $R^{17}$, $R^{18}$ and $R^{25}$ may be substituted, may be linear or, when there is a sufficient number (i.e. three) of carbon atoms, be branched and/or cycloalkyl or cycloalkoxy with carbon ranges as defined above, and wherein, when there is a sufficient number (i.e. four) of carbon atoms, such alkyl and alkoxy groups may also be part cycloalkylacyclic or cycloalkoxy/acyclic with carbon ranges as defined above, and wherein such alkyl and alkoxy groups may, when there is a sufficient number (i.e. two) of carbon atoms, be interrupted by oxygen and/or substituted by one or more fluoro groups; and wherein alkylene groups that A and B may represent, and —$(CH_2)$— containing groups that $R^1$, $R^7$, $R^8$, $R^{10}$, $R^{11}$, $R^{13}$, $R^{14}$, $R^{15}$, $R^{16}$, $R^{17}$, $R^{18}$, $R^{25}$, A, B and D may include, may be linear or, when there is a sufficient number (i.e. two) of carbon atoms, be branched, and wherein such alkylene groups and —$(CH_2)$— containing chains may, when there is a sufficient number (i.e. two) of carbon atoms, be interrupted by oxygen, provided that when $R^{5a}$ and $R^{5b}$ both represent H, then D does not represent H or OH, or a compound of formula XVII,

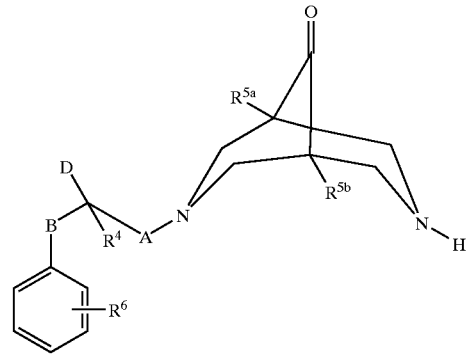

wherein $R^4$, $R^{5a}$, $R^{5b}$, $R^6$, A, B and D are as defined in claim 1, provided that when $R^{5a}$ and R b both represent H, then D does not represent H or OH, which comprises reaction of a compound of formula XXIX,

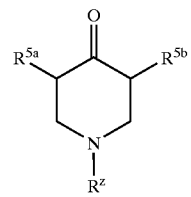

wherein $R^Z$ represents H or —C(O)$XR^1$ and $R^1$, $R^{5a}$, $R^{5b}$ and X are as defined in claim 1 with a compound of formula XXX,

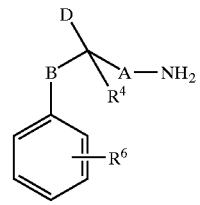

wherein $R^4$, $R^6$, A, B and D are as defined in claim 1, in the presence of a formaldehyde.

22. A method as claimed in claim 15, wherein the arrhythmia is an atrial or a ventricular arrhythmia.

* * * * *